United States Patent
Zdeblick et al.

(10) Patent No.: US 6,514,260 B1
(45) Date of Patent: Feb. 4, 2003

(54) METHODS AND INSTRUMENTS FOR LAPAROSCOPIC SPINAL SURGERY

(75) Inventors: Thomas Zdeblick, Middletown, WI (US); Thomas V. McGahan, Memphis, TN (US); Steven D. DeRidder, Bartlett, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 09/525,972

(22) Filed: Mar. 15, 2000

(51) Int. Cl.[7] .............................................. A61B 17/56
(52) U.S. Cl. ....................................................... 606/90
(58) Field of Search .............................. 606/61, 53, 86, 606/90, 80, 96, 99, 104, 105, 108; 623/17.16, 902

(56) References Cited

U.S. PATENT DOCUMENTS

| | | |
|---|---|---|
| 3,750,667 A | 8/1973 | Pshenichny et al. |
| 4,545,374 A | 10/1985 | Jacobson |
| 4,654,030 A | 3/1987 | Moll et al. |
| 4,931,042 A | 6/1990 | Holmes et al. |
| 5,158,543 A | 10/1992 | Lazarus |
| 5,195,541 A | 3/1993 | Obenchain |
| 5,224,952 A | 7/1993 | Deniega et al. |
| 5,256,149 A | 10/1993 | Banik et al. |
| 5,273,026 A | 12/1993 | Wilk |
| 5,306,239 A | 4/1994 | Gurmarnik et al. |
| 5,334,150 A | 8/1994 | Kaali |
| 5,376,076 A | 12/1994 | Kaali |
| 5,407,433 A | 4/1995 | Loomas |
| 5,439,449 A | 8/1995 | Mapes et al. |
| 5,484,437 A | 1/1996 | Michelson |
| 5,534,009 A | 7/1996 | Lander |
| 5,551,947 A | 9/1996 | Kaali |
| 5,569,205 A | 10/1996 | Hart et al. |
| 5,569,290 A | 10/1996 | McAfee |
| 5,584,847 A | * 12/1996 | Duluco et al. ............. 606/185 |
| 5,645,549 A | 7/1997 | Boyd et al. |
| 5,797,909 A | 8/1998 | Michelson |
| 5,843,040 A | * 12/1998 | Exline .......................... 604/164 |
| 5,954,635 A | * 9/1999 | Foley et al. ................ 600/114 |
| 6,004,326 A | 12/1999 | Castro et al. |
| 6,113,602 A | * 9/2000 | Sand ............................. 606/61 |
| 6,171,339 B1 | * 1/2001 | Houfburg et al. ............. 606/61 |
| 6,228,022 B1 | * 5/2001 | Friesem et al. ............. 600/204 |

FOREIGN PATENT DOCUMENTS

| | | |
|---|---|---|
| WO | WO 93/14801 | 8/1993 |
| WO | WO 94/17759 | 8/1994 |
| WO | WO 97/30666 | 8/1997 |
| WO | WO 98/04202 | 2/1998 |

OTHER PUBLICATIONS

Sofamor Danek The Spine Specialist (1995), Sofamor Danek Laparoscopic Bone Dowel System Laparoscopic Surgical Procedure.
Sofamor Danek The Spine Specialist, Surgical Technique Using Bone Dowel Instrumentation for Anterior Endoscopic Approach.
Sofamor Danek, The Spine Specialist, Laparoscopic Bone Dowel Surgical Technique, 1995.

* cited by examiner

*Primary Examiner*—Eduardo C. Robert
(74) *Attorney, Agent, or Firm*—Woodard, Emhardt, Naughton, Moriarty & McNett LLP

(57) ABSTRACT

Surgical techniques and instruments are provided for performing surgical procedures in a disc space. The instrument includes a sleeve having a distal end and an opposite proximal end and a working channel extending therebetween. The working channel includes a first portion and an adjacent second portion configured to receive surgical instruments therethrough. A cap member is secured to the sleeve at the proximal end. The cap member has a sealable access port substantially aligned with a corresponding one of the first or second portions. The cap member is movable with respect to the sleeve to substantially align the access port with the other of the first and second portions while the working channel remains sealed. Various techniques using various surgical instruments in laparoscopic procedures are also disclosed.

94 Claims, 18 Drawing Sheets

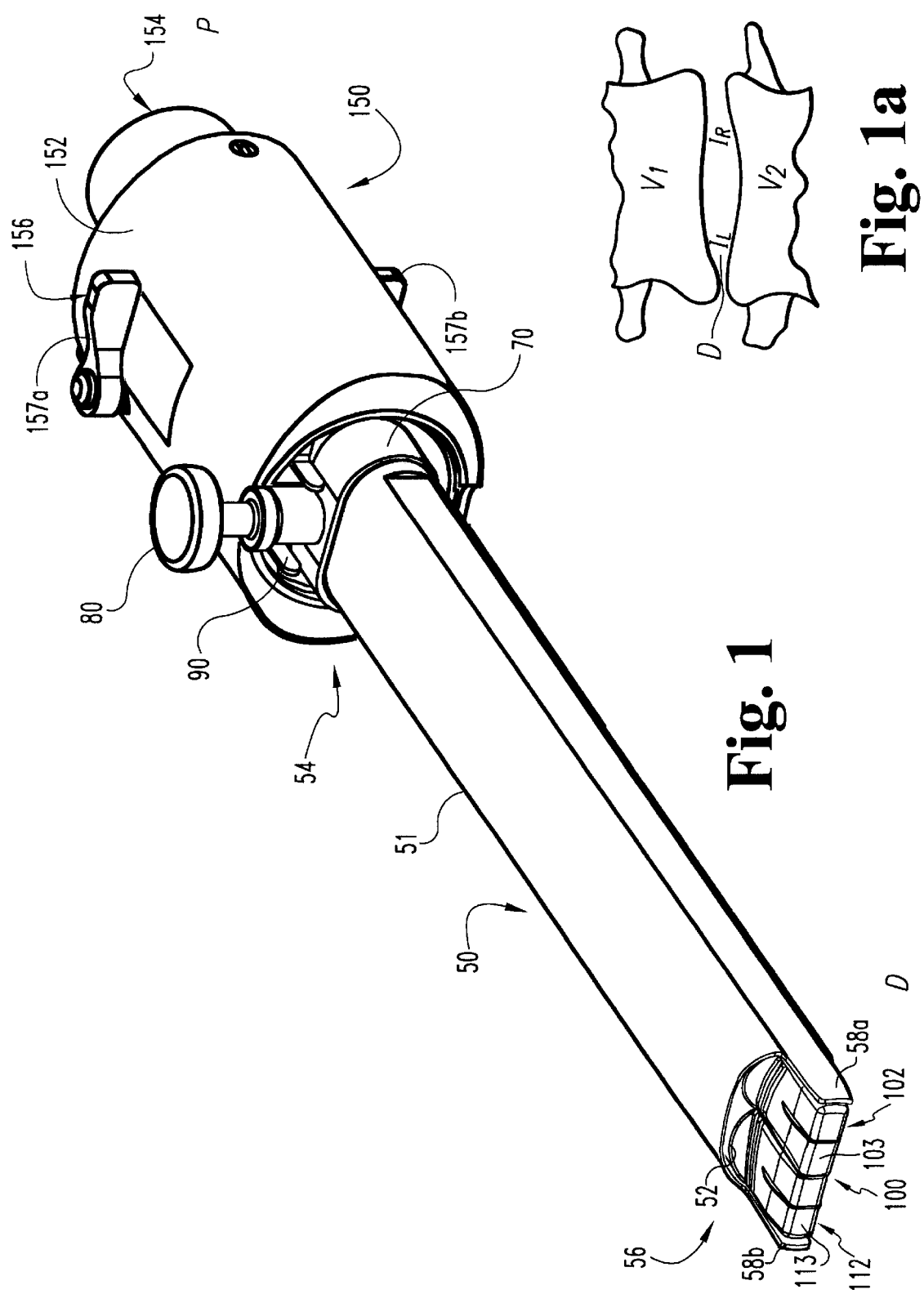

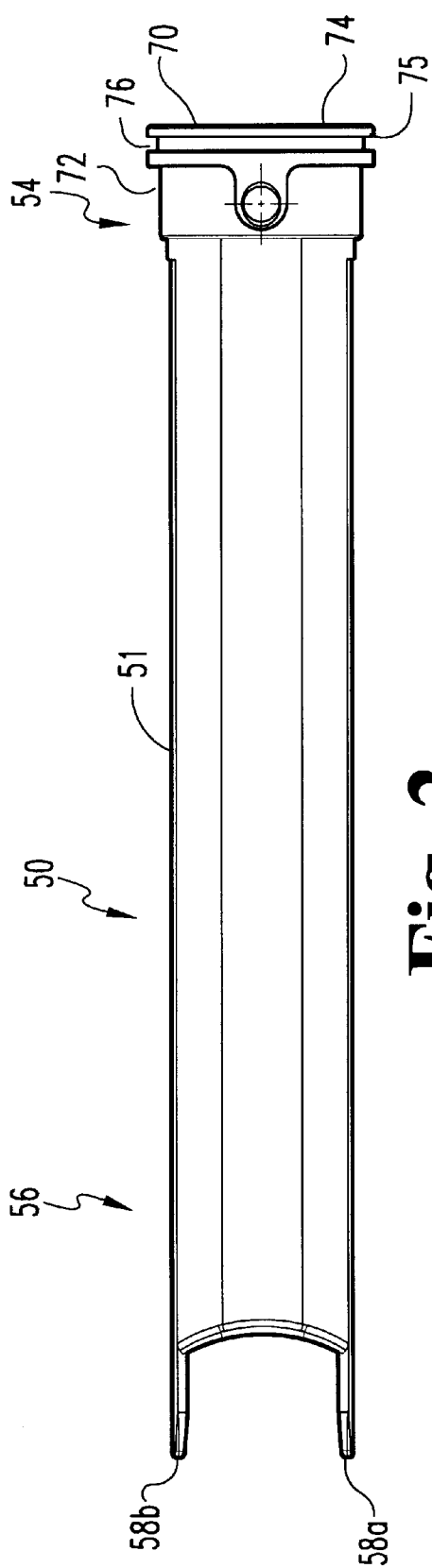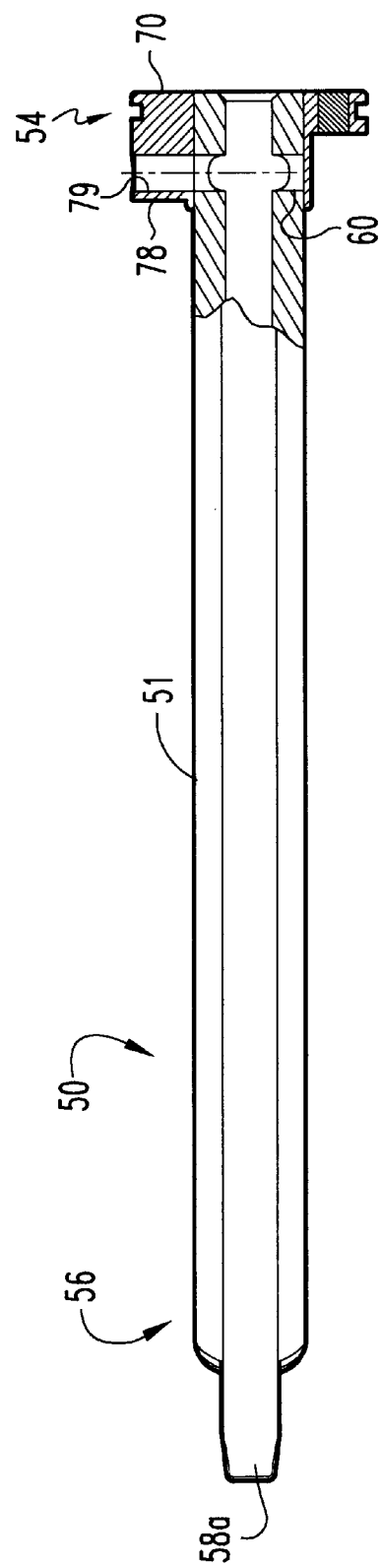

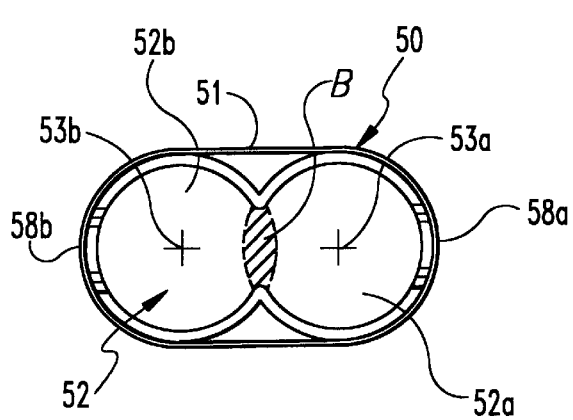
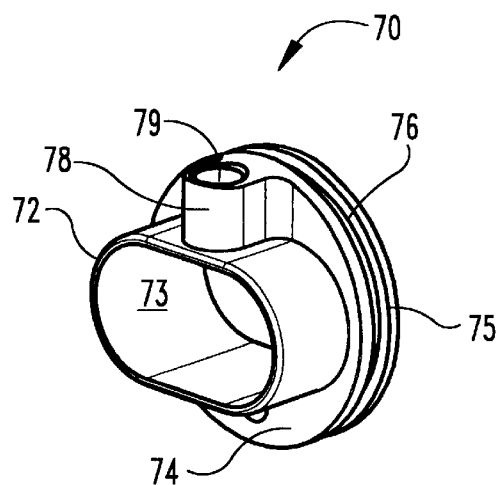
Fig. 4    Fig. 5
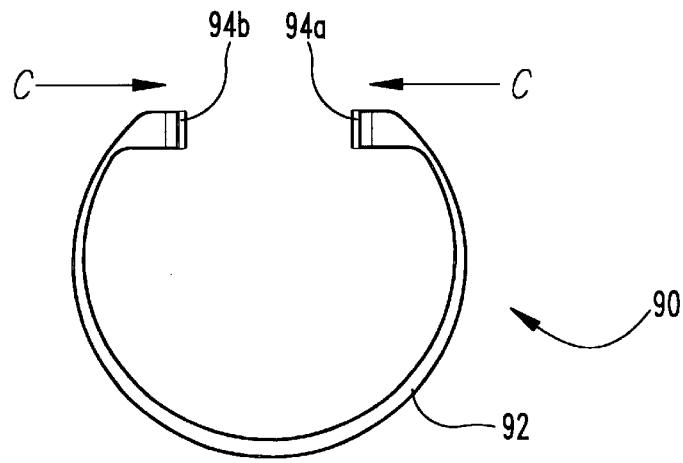
Fig. 6
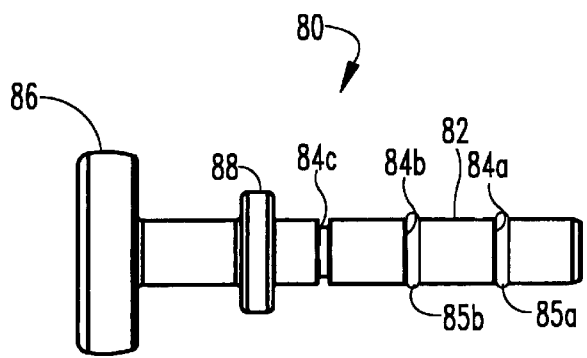
Fig. 7

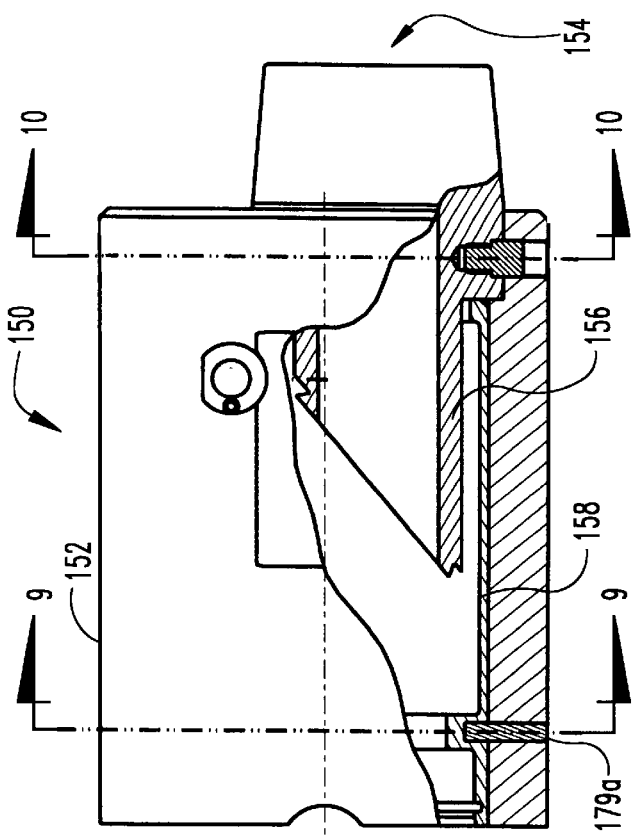
Fig. 8
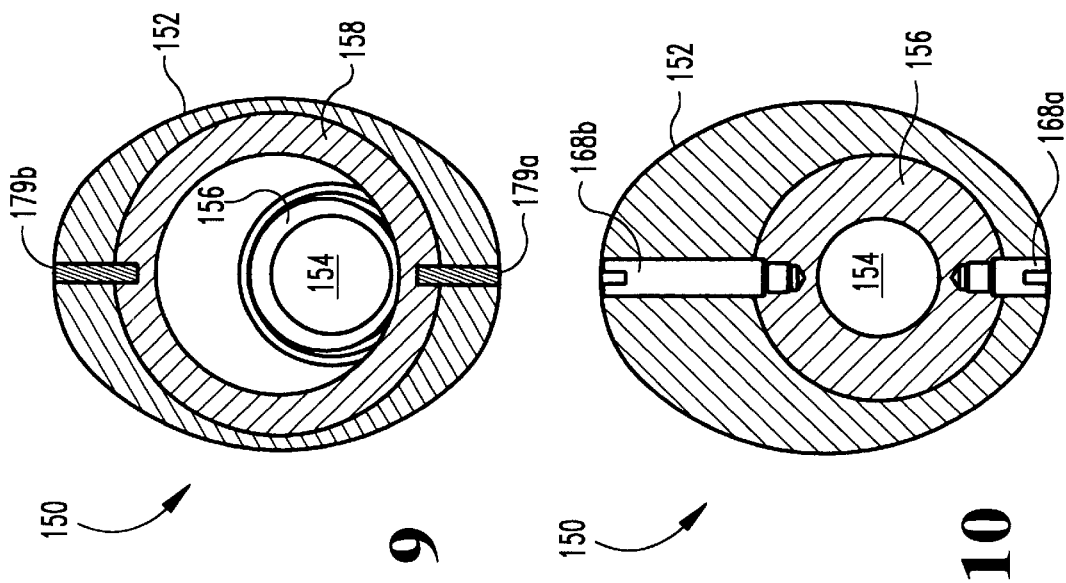
Fig. 9
Fig. 10

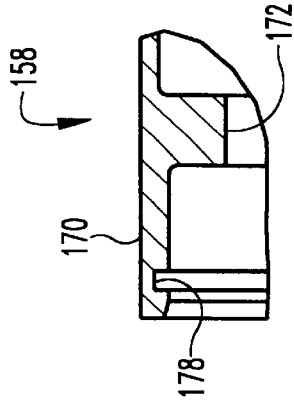
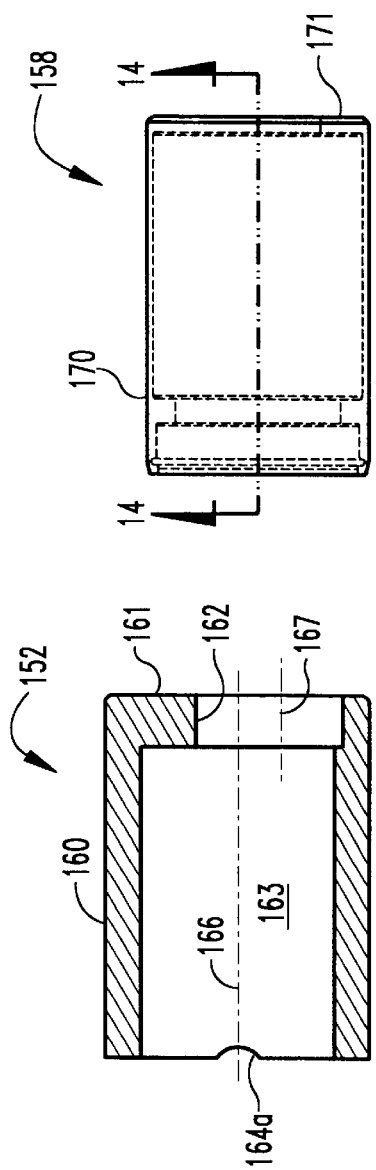
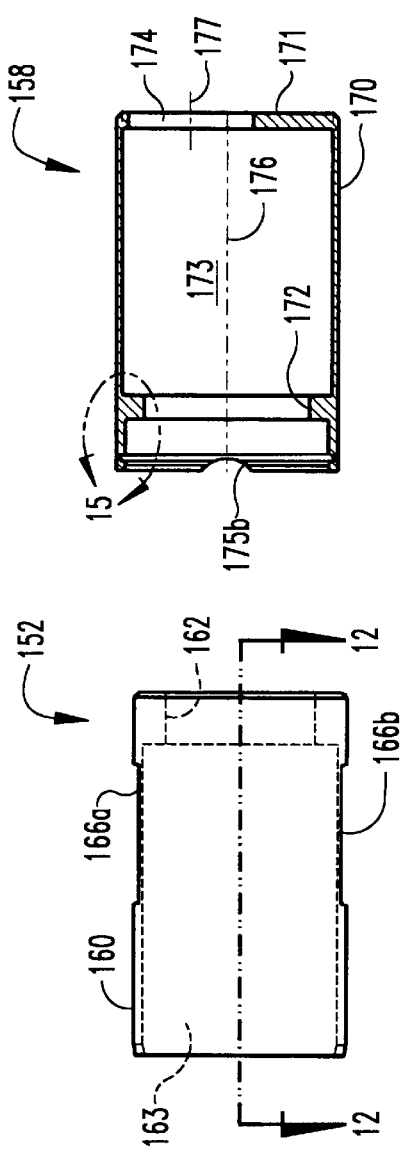

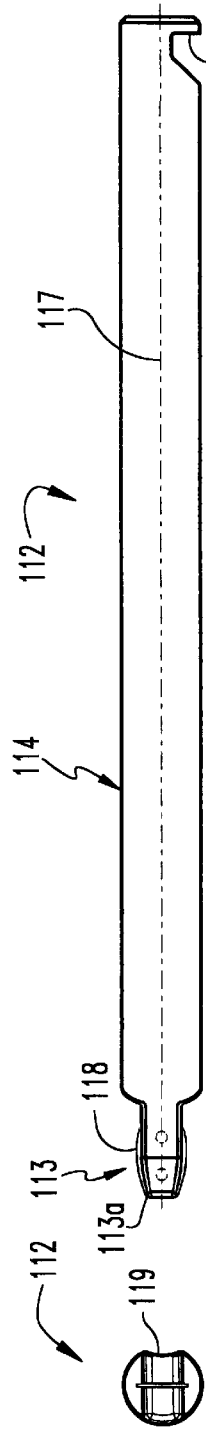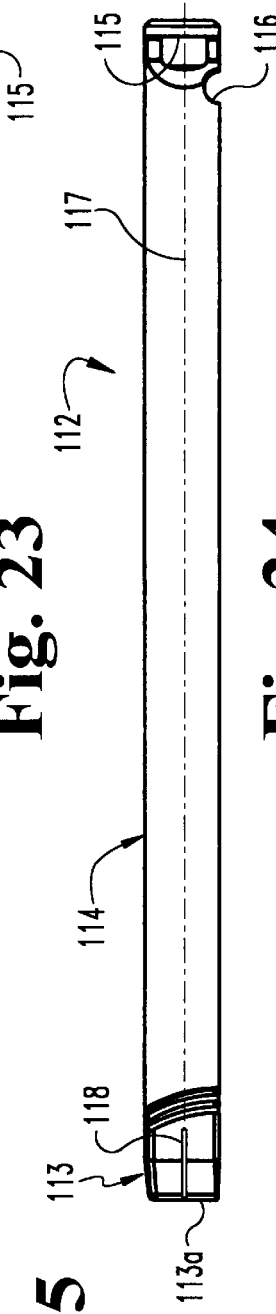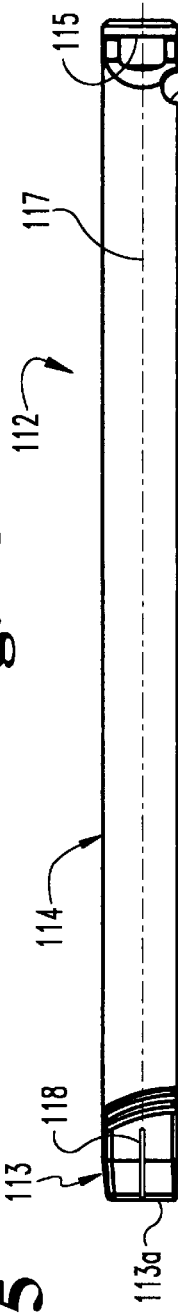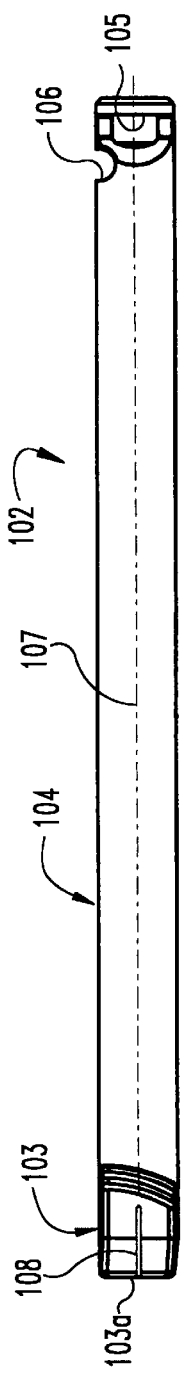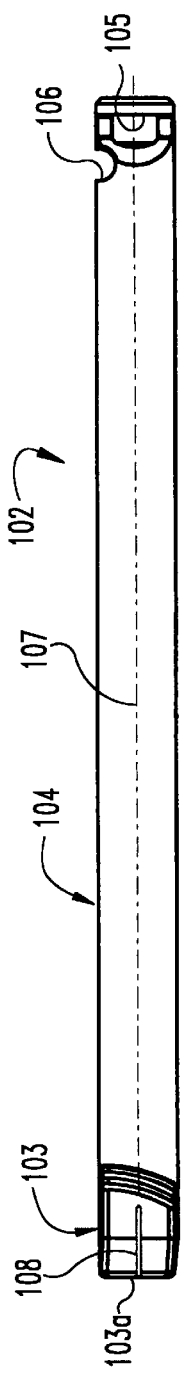

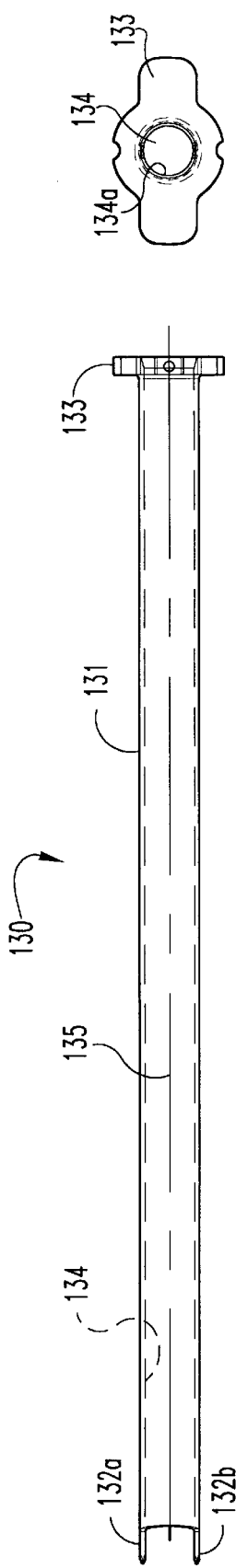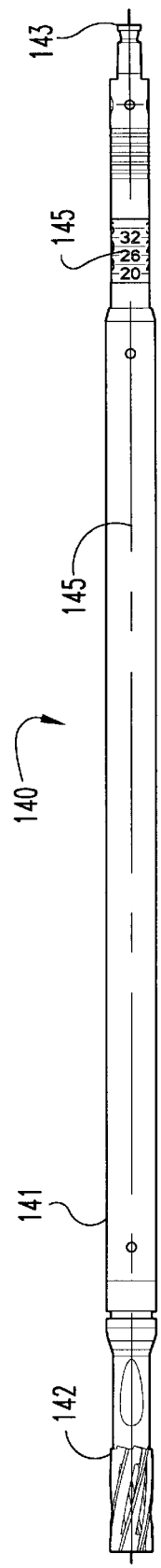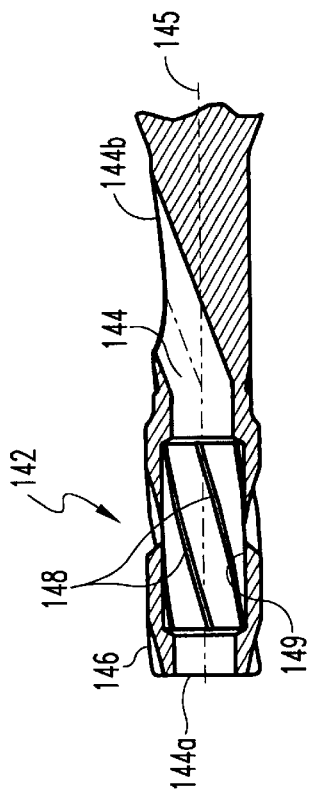

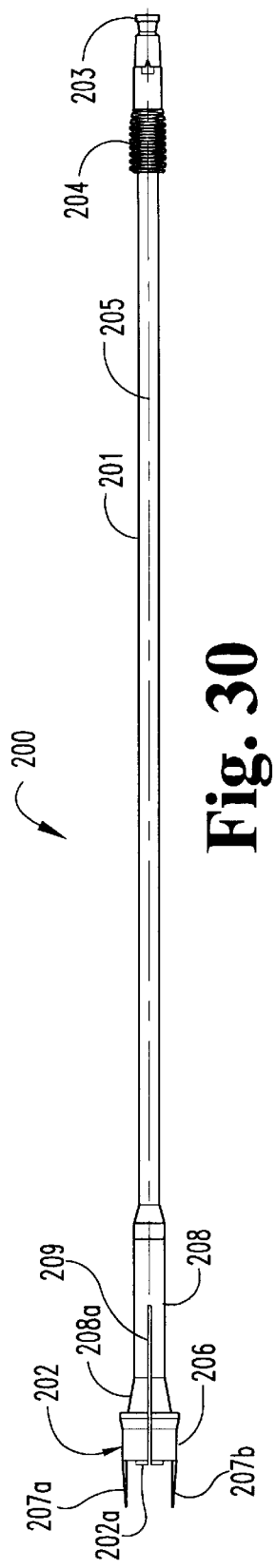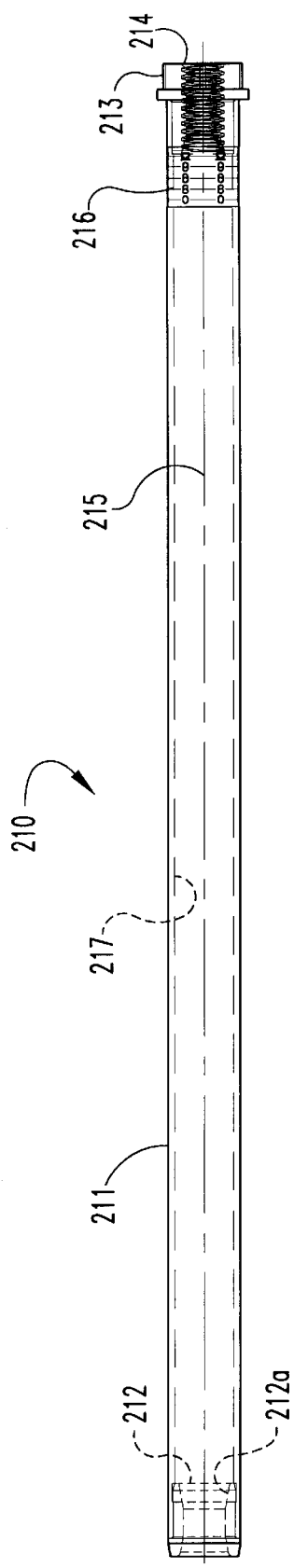
Fig. 30
Fig. 31

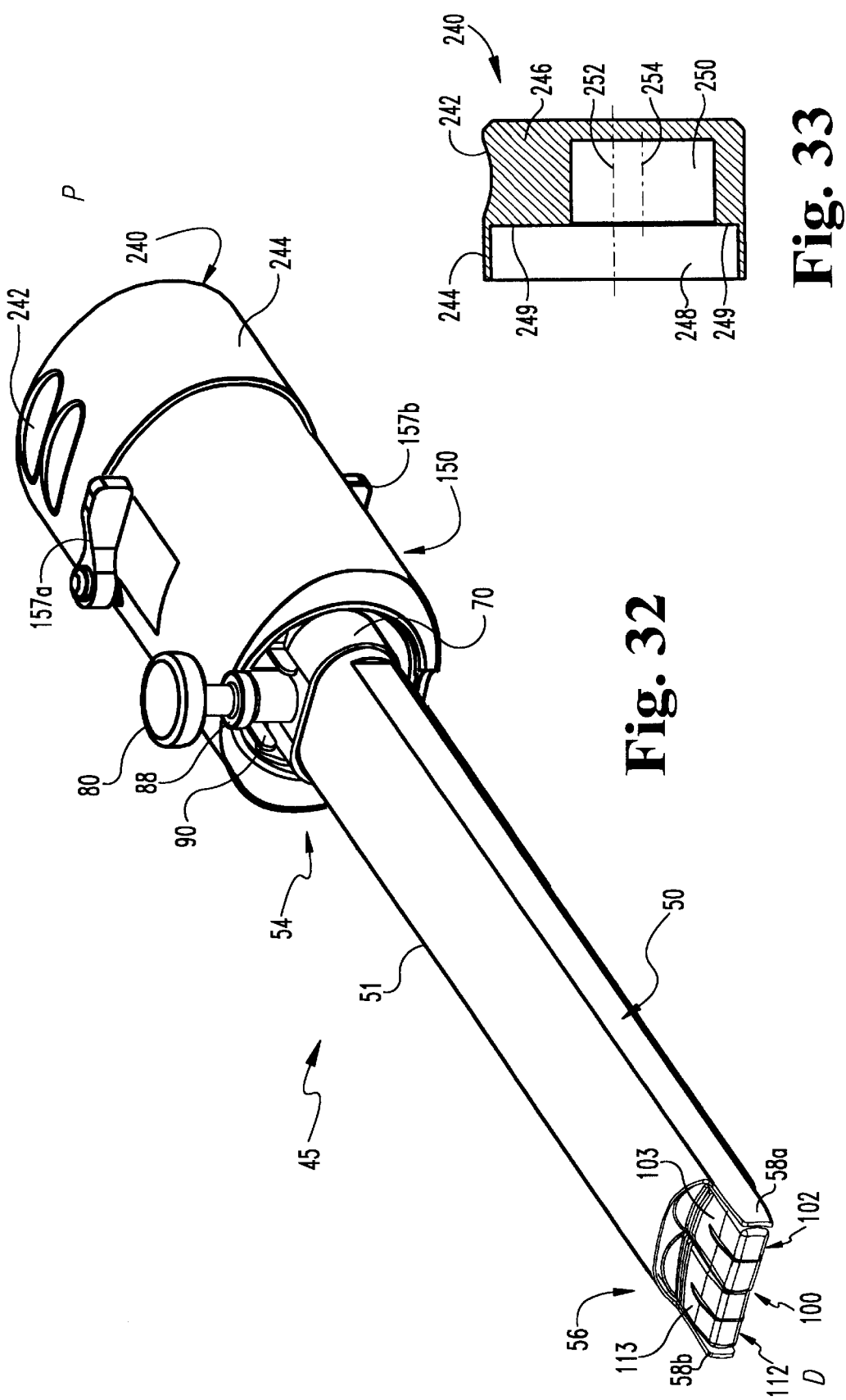

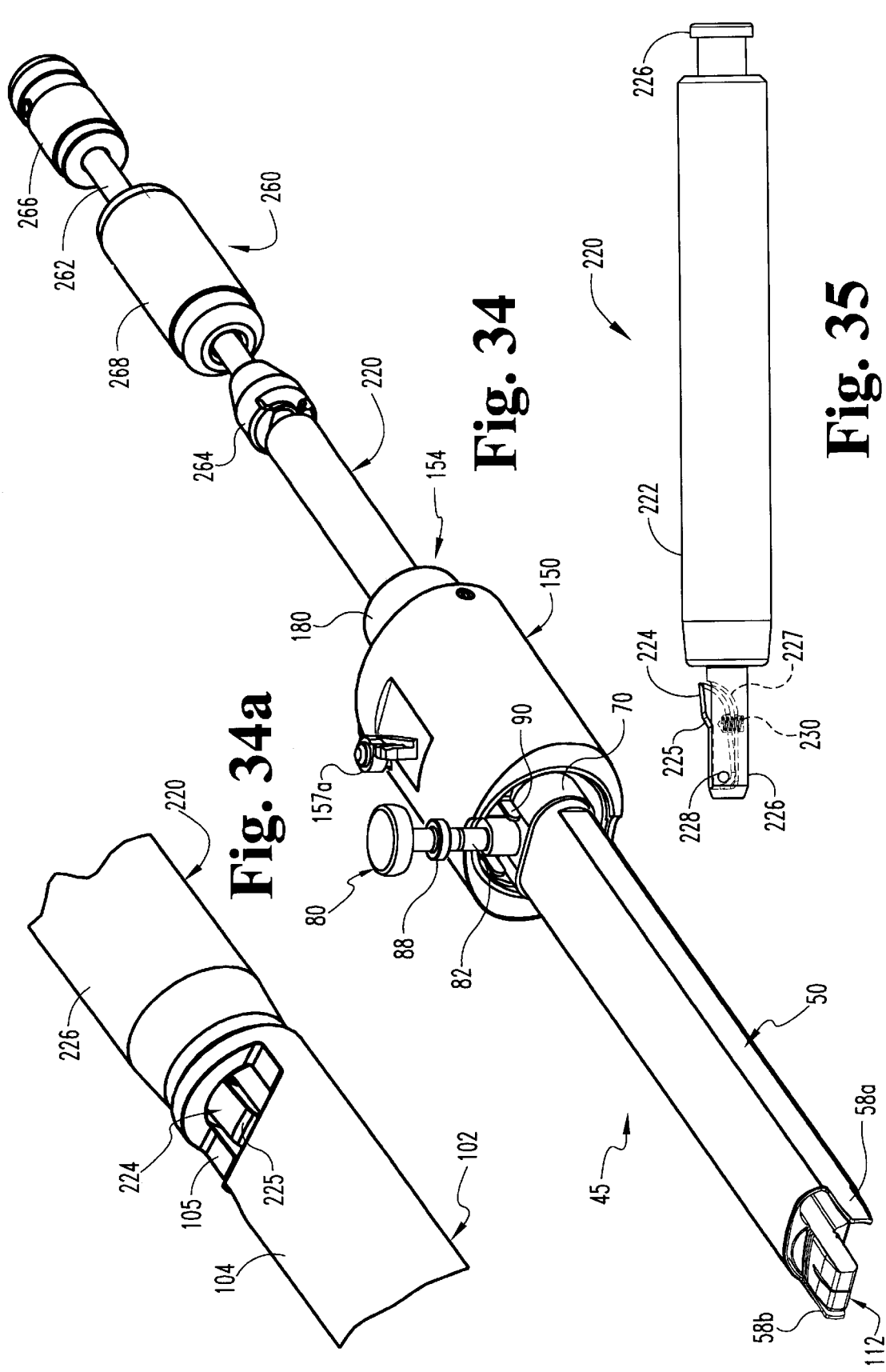

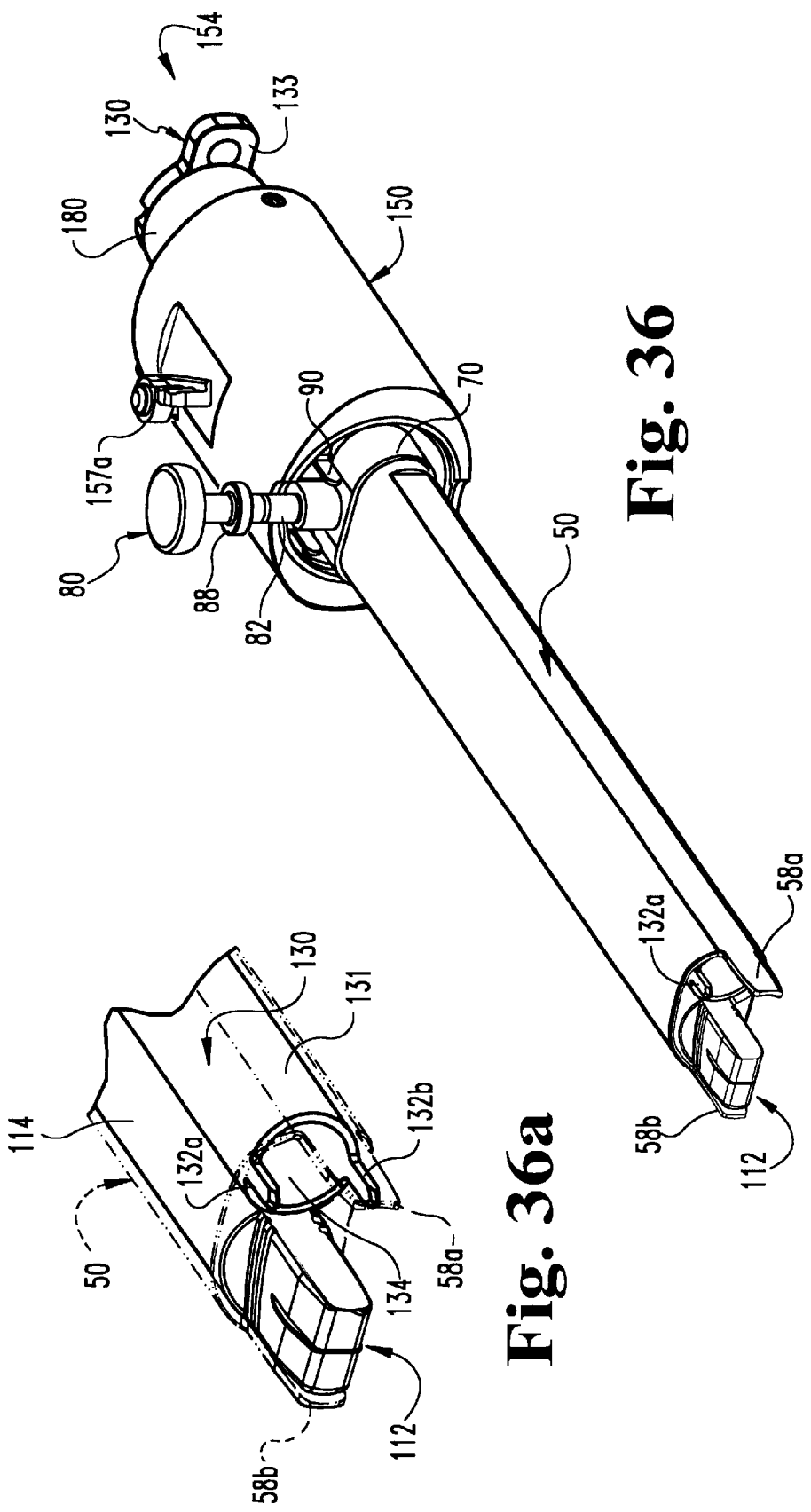

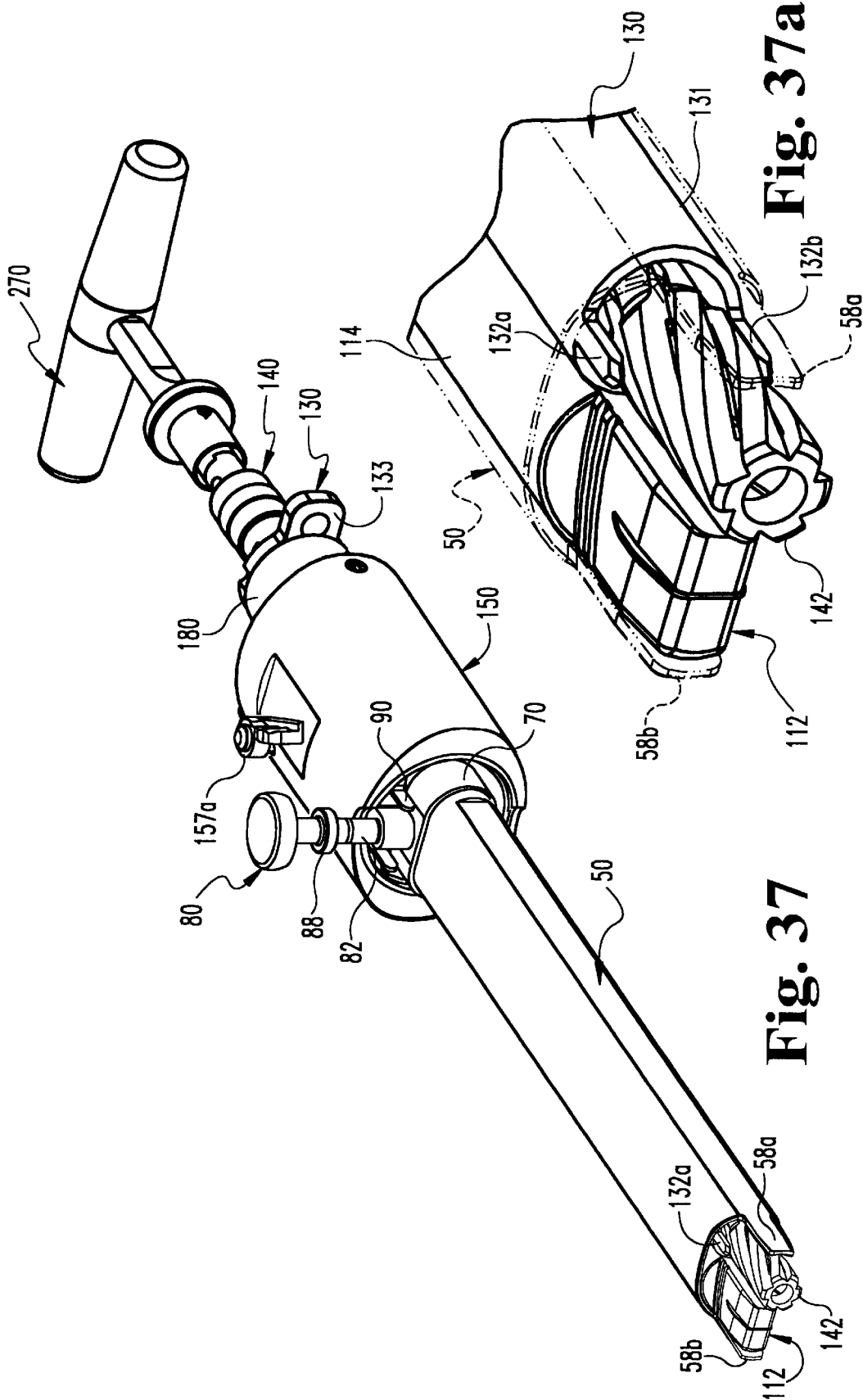

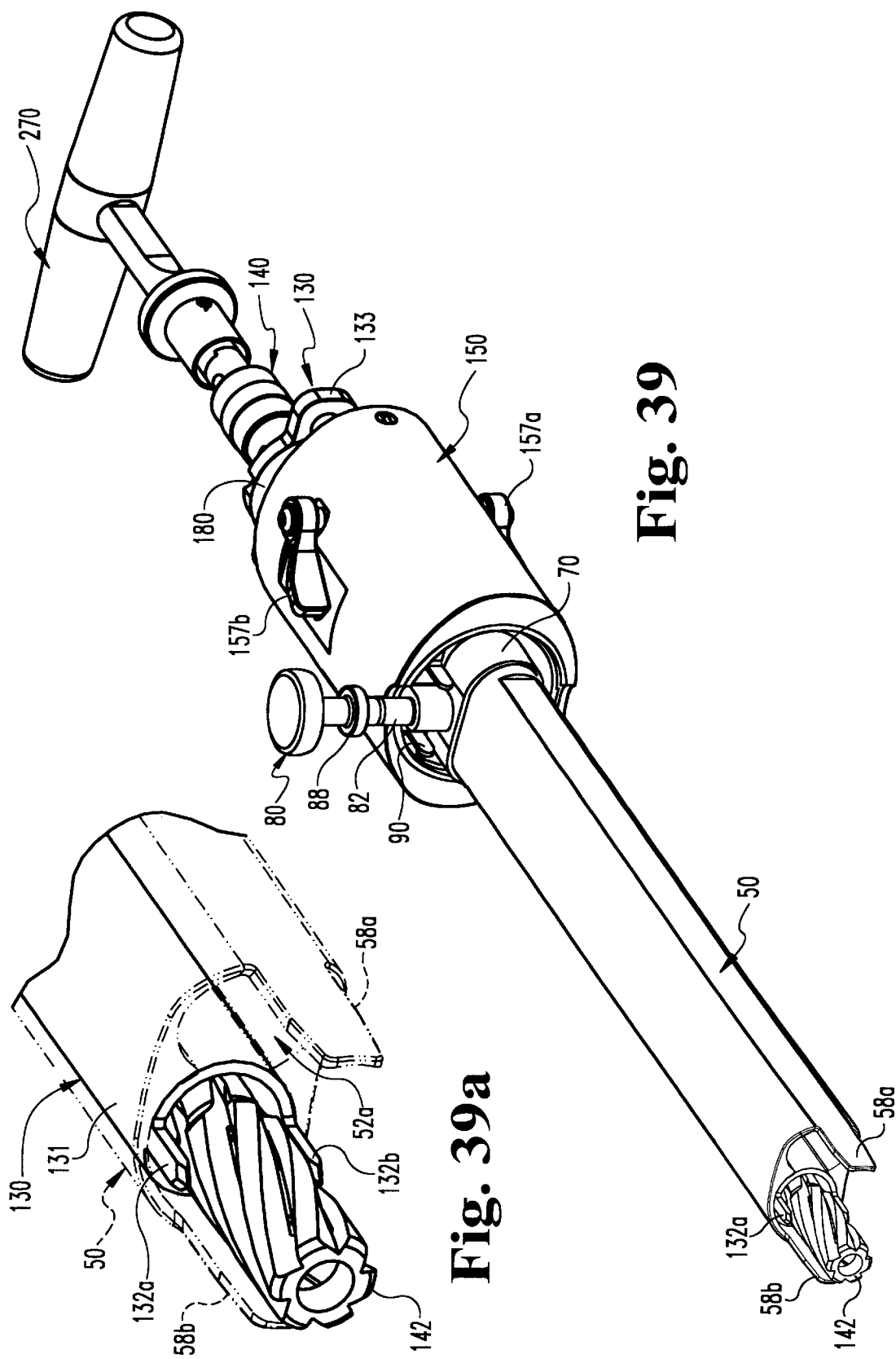

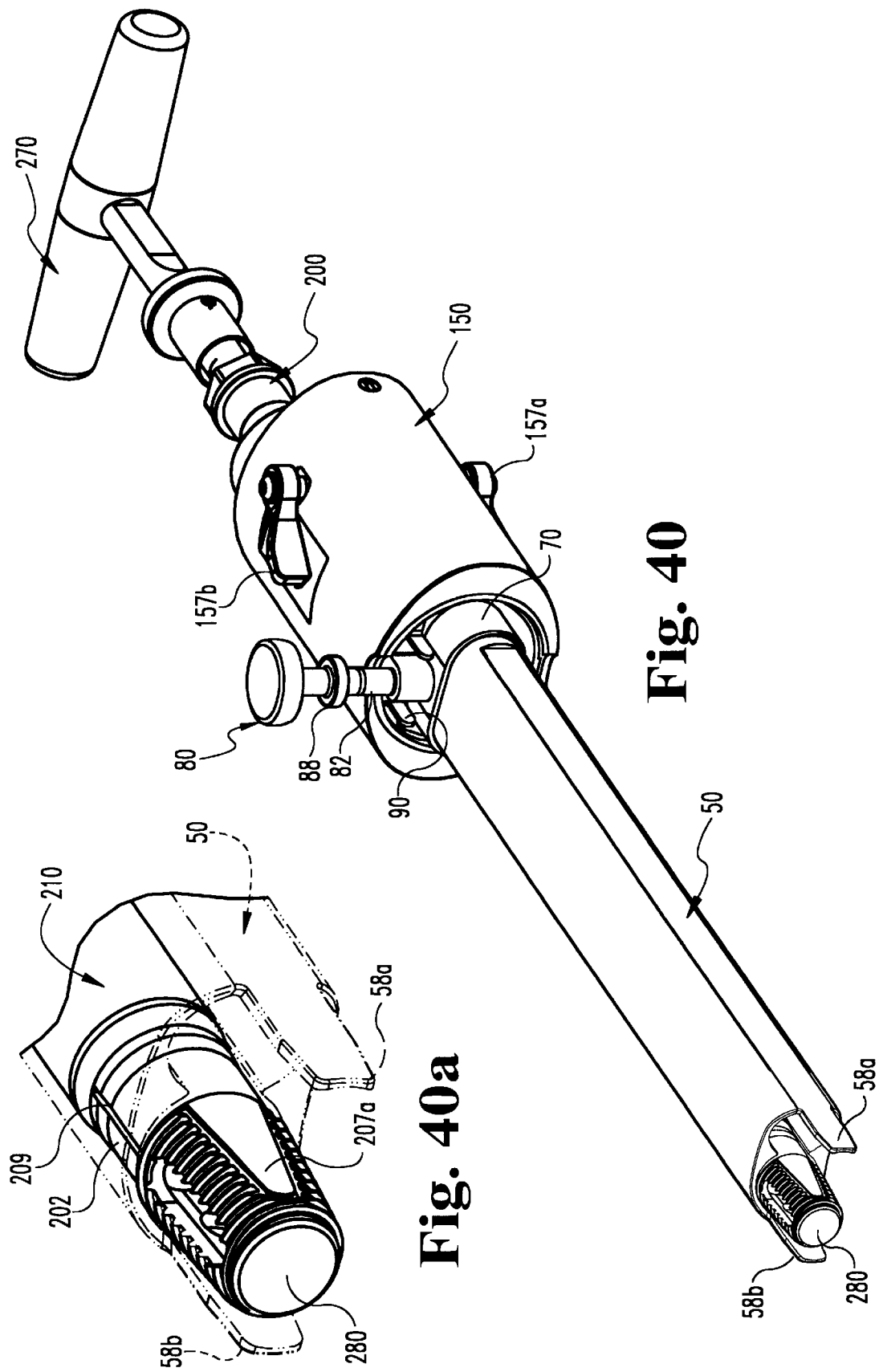

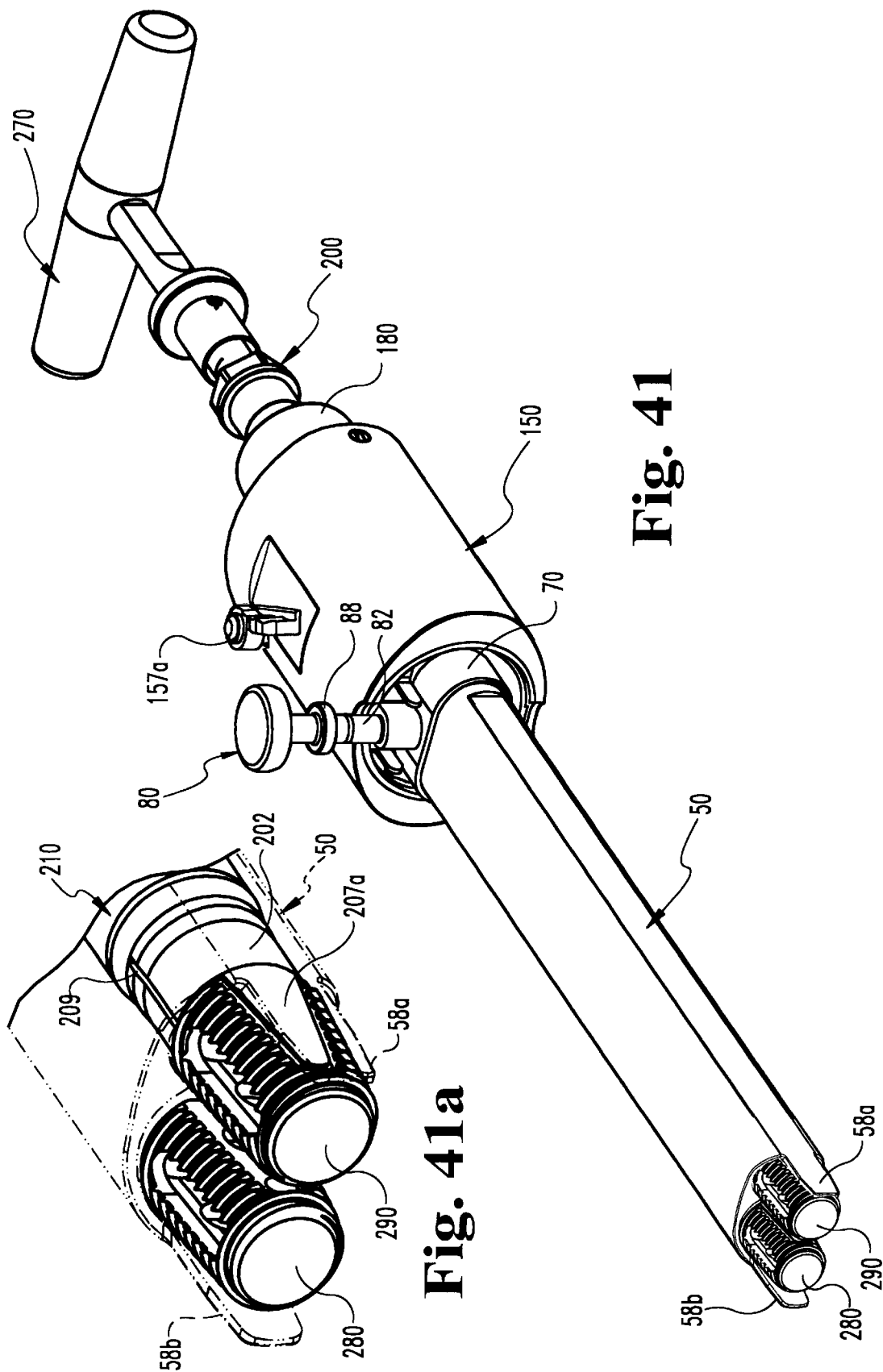

METHODS AND INSTRUMENTS FOR LAPAROSCOPIC SPINAL SURGERY

BACKGROUND OF THE INVENTION

The present invention relates generally to methods and instruments for performing spinal surgery. Specifically, the invention concerns laparoscopic techniques and instruments to perform spinal surgeries.

The use of surgical techniques to correct the causes of low back pain, such as spinal injuries and deformities, has steadily increased over the last several years. One common procedure for relieving pain from the above-described problems is a discectomy, or surgical removal of a portion or all of an intervertebral disc, followed by implantation of a device between the adjacent vertebrae, such as a vertebral implant or fusion device. Typically, implantation of such a device is intended to promote bony fusion between the adjacent vertebral bodies.

Various surgical methods have been devised for implantation of devices into a subject disc space. For example, PCT International Publication No. WO 97/30666 to Zdeblick et al. discloses laparoscopic surgical techniques and instruments for preparing a disc space for implantation of fusion devices or implants. The laparoscopic instrumentation provides a sealed working channel to the disc space through which the disc space is distracted, the vertebral endplates and surrounding discs are reamed, and the vertebral implant inserted, all through a laparoscopic port engaged to the end of the sleeve. In this technique, a single sleeve is alternately placed at bilateral locations on the disc space through a single incision in the skin for insertion of a pair of fusion devices or vertebral implants at each location. A switching sleeve extends through the outer sleeve of the laparoscope to protect the tissue at the surgical site as the outer sleeve of the laparoscope is moved between bilateral locations. In order to move the outer sleeve, the switching sleeve is inserted and then the distractor fingers of the outer sleeve are withdrawn from the disc space at the first bilateral location. The outer sleeve and the switching sleeve are then manipulated through the skin to the second bilateral location. The techniques and instruments of the '666 publication suffer from the disadvantage of requiring multiple manipulations of vessels and tissue adjacent the vertebral bodies to perform the procedure. Multiple manipulation of the vessels and tissues may increase the overall time of the procedure and increase the risk of damage to the vessels.

While the above described technique represents a significant advance over prior surgical procedures for spinal surgery, a need for improvement remains. In particular, procedures and instruments are required that minimize trauma to tissue surrounding the surgical site while allowing surgical procedures to be performed, such as spinal disc space preparations, implant insertion, and the like. There is also a need for instruments and techniques that maintain a sealed working channel during surgical procedures performed at multiple locations. The present invention is directed to these needs, among others.

SUMMARY OF THE INVENTION

The present invention includes surgical instruments and techniques for performing procedures at adjacent disc space locations in a generally sealed environment through a cap member having an access port alignable with a corresponding one of the disc space locations.

In one aspect of the invention, a method for performing a surgical procedure in a disc space between adjacent vertebrae is provided. The method includes accessing the disc space through skin and tissue of the patient. An instrument assembly including a sleeve is provided that has a distal end and an opposite proximal end. The sleeve defines a working channel between the distal and proximal ends. The working channel has a first portion and an adjacent second portion, and the working channel is sealable by a cap member secured to the proximal end of the sleeve. Preferably, the cap member has a sealable access port alignable with the first portion of the working channel. In a preferred aspect, the sleeve is advanced into the patient until the proximal end of the sleeve is positioned adjacent the disc space. The cap member can then be positioned with the access port aligned with the first portion or the second portion of the working channel while the sealed working channel is maintained.

Preferably, the disc space is prepared through the access port and first portion of the working channel. An implant may then be inserted through the access port and first portion with the working channel remaining substantially sealed. In a most preferred aspect, the access port is moved into alignment with the second portion of the working channel and the disc space is prepared for implant insertion through the access port and the second portion with the working channel remaining substantially sealed.

According to another aspect of the invention, an apparatus for performing a surgical procedure in the disc space between adjacent vertebrae of a patient is provided. The apparatus includes a sleeve having a distal end, an opposite proximal end, and a sealable working channel extending therethrough. The working channel has a first portion and an adjacent second portion each configured to receive surgical instruments therethrough. A cap member is secured to the second end of the sleeve. The cap member has an access port that seals the working channel when closed. The access port is alignable with a corresponding one of the first or second portions. The cap member can be moved with respect to the sleeve to substantially align the access port with the other of the first and second portions while the working channel remains sealed.

According to another aspect of the invention, an apparatus for performing a surgical procedure in the disc space between adjacent vertebrae of a patient is provided. The apparatus has a sleeve with a distal end, an opposite proximal end, and a working channel extending therebetween. The sleeve has a non-circular perimeter and a flange ring having a circular perimeter is secured at the proximal end of the sleeve. A cap member is secured to the flange ring at the proximal end, and has an access port. The cap member is movable about the flange ring to align the access port with a portion of the working channel while the working channel remains sealed.

According to yet another aspect of the invention, an apparatus for use in preparing a disc space for insertion of a vertebral implant is provided. The apparatus includes a sleeve that defines a working channel extending between a distal end and a proximal end. The working channel has a first portion and an adjacent second portion. A pair of distractors are each disposed in a corresponding one of the first and second portions. The distractors are coupled to the sleeve. Each of the distractors has a distractor tip for distracting the disc space when inserted therein. A cap member secured to the proximal end of the sleeve has a sealable access port for sealing the working channel. An impactor cap positionable over the cap member receives a driving force to insert the distractors in the disc space with the working channel sealed.

Other objects, advantages, features, embodiments, aspects and benefits can be discerned from the following written description and the accompanying figures.

BRIEF DESCRIPTION OF THE DRAWINGS

FIG. 1 is a perspective view of a surgical instrument assembly according to one aspect of the present invention.

FIG. 1a is an elevational view of a spinal column segment.

FIG. 2 is a top plan view of the guide sleeve comprising a portion of the surgical instrument assembly of FIG. 1.

FIG. 3 is a partial section, partial elevational side view of the guide sleeve of FIG. 2.

FIG. 4 is a left-hand end view of the guide sleeve of FIG. 2.

FIG. 5 is a perspective view of the flange ring comprising a portion of the guide sleeve of FIG. 2.

FIG. 6 an elevational view of the spring clip comprising a portion of the surgical instrument assembly of FIG. 1.

FIG. 7 is an elevational view of the lock pin comprising a portion of the surgical instrument assembly of FIG. 1.

FIG. 8 is a partial section, partial elevational view the cap member comprising a portion of the surgical instrument assembly of FIG. 1.

FIG. 9 is a cross-sectional view taken through line 9—9 of FIG. 8.

FIG. 10 is a cross-sectional view taken through line 10—10 of FIG. 8.

FIG. 11 is a side elevational view of the housing comprising a portion of the cap member of FIG. 8.

FIG. 12 is a cross-sectional view taken through line 12—12 of FIG. 11.

FIG. 13 is a side elevational view of the insert member comprising a portion of the cap member of FIG. 10.

FIG. 14 is a cross-sectional view taken along line 14—14 of FIG. 13.

FIG. 15 is an enlarged detail view of a portion of FIG. 13.

FIG. 20 is a side elevational view of a first distractor comprising a portion of the instrument of FIG. 1.

FIG. 21 is a top plan view of the distractor of FIG. 20.

FIG. 22 is a left hand end view of the distractor of FIG. 20.

FIG. 23 is a side elevational view of a second distractor comprising a portion of the surgical instrument assembly of FIG. 1.

FIG. 24 is a top plan view of the distractor of FIG. 23.

FIG. 25 is a left hand end view of the distractor of FIG. 23.

FIG. 26 is a side elevational view of a reaming sleeve usable with the surgical instrument assembly of FIG. 1.

FIG. 27 is a right hand end view of the sleeve of FIG. 26.

FIG. 28 is an elevational view of a reamer insertable through the sleeve of FIG. 26.

FIG. 29 is an enlarged detail view of the cutting end of the reamer of FIG. 28.

FIG. 30 is an elevational view of an implant inserter usable with the surgical instrument assembly of FIG. 1.

FIG. 31 is an elevational view of an implant inserter sleeve usable with the implant inserter of FIG. 30.

FIG. 32 is a perspective view of the surgical instrument assembly of FIG. 1 with an impactor cap placed on the cap member.

FIG. 33 is a cross-sectional view of the impactor cap of FIG. 32.

FIGS. 34 and 34a are a perspective view and an enlarged detail view, respectively, of the surgical instrument assembly of the present invention with the first distractor connected to a distractor remover.

FIG. 35 is an elevational view of a distractor remover coupler comprising a portion of the distractor remover of FIG. 34.

FIGS. 36 and 36a are a perspective view and an enlarged detail view, respectively, of the surgical instrument assembly of the present invention with the first distractor removed.

FIGS. 37 and 37a are a perspective view and an enlarged detail view, respectively, of the surgical instrument assembly of the present invention with the first distractor removed and the reaming sleeve and reamer inserted through the guide sleeve.

FIGS. 39 and 39a are a perspective view and an enlarged detail view, respectively, of the surgical instrument assembly of the present invention with the cap member rotated, the second distractor removed, and the reaming sleeve and reamer inserted through the guide sleeve.

FIGS. 40 and 40a are a perspective view and an enlarged detail view, respectively, of the surgical instrument assembly of the present invention with an implant being inserted through the guide sleeve at a first location.

FIGS. 41 and 41a are a perspective view and an enlarged detail view, respectively, of the surgical instrument assembly of the present invention with the cap member rotated to its position of FIG. 34 and a second implant being inserted through the guide sleeve at a second location.

DESCRIPTION OF THE PREFERRED EMBODIMENTS

Figure 16:
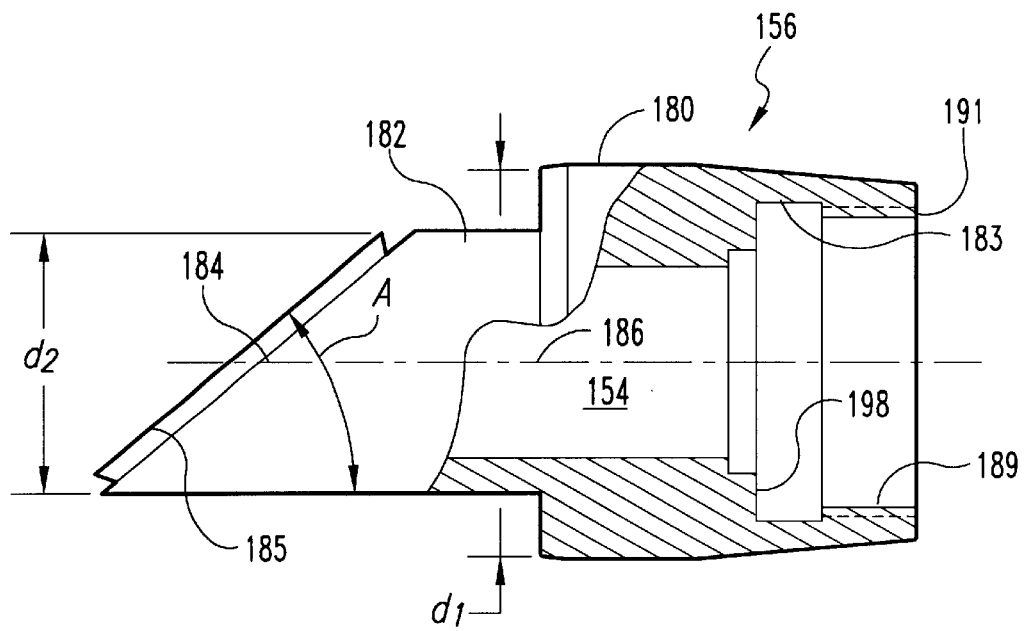
FIG. 16 is a partial section, partial elevational view of the valve member comprising a portion of the cap member of FIG. 8.
Figure 17:
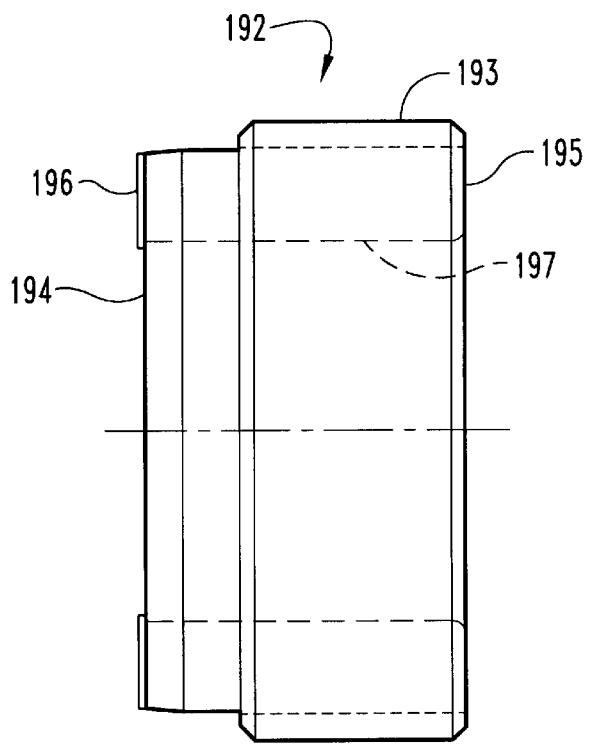
FIG. 17 is an enlarged side elevational view of the valve insert insertable into the valve member of FIG. 16.

For the purposes of promoting an understanding of the principles of the invention, reference will now be made to the embodiment illustrated in the drawings and specific language will be used to describe the same. It will nevertheless be understood that no limitation of the scope of the invention is thereby intended. Any such alterations and further modifications in the illustrated devices, and any such further applications of the principles of the invention as illustrated herein are contemplated as would normally occur to one skilled in the art to which the invention relates.

A surgical instrument assembly in accordance with the present invention is illustrated in FIG. 1 and designated generally at 45. Surgical instrument assembly 45 is particularly useful for accessing and preparing, as show in FIG. 1a, a disc space S for insertion of vertebral implants or fusion devices between upper vertebral body V1 and lower vertebral body V2. In one aspect of the present invention, the surgical instrument assembly allows surgical procedures to be performed under a relatively sealed and protected passageway in an insufflated environment within the body cavity. This prevents leakage of abdominal distension fluids into the working channel and disc space and aids vision of the surgical site. The surgical procedure described herein is performed via an anterior approach to the spine. However, the surgical instruments of the present invention are not limited to such an approach, and may find application in lateral, anterolateral, posterior, and postero-lateral approaches as well. Additionally, the surgical instruments of the present invention may find application at all vertebral segments of the spine, and in areas other than spinal surgery.

Assembly 45 includes a cap member 150 secured to a guide sleeve 50. Guide sleeve 50 has a working channel 52 extending between proximal end 54 and distal end 56 with a distractor assembly 100 disposed in working channel 52. In the description that follows, proximally refers to the direction indicated by letter "P" and distally refers to the direction indicated by letter "D." Guide sleeve 50 is further depicted in FIGS. 2–4, and as described more fully below, receives various tools and surgical instruments therethrough in order to perform surgical procedures on the spine. Sleeve 50 has a length sufficient to extend from the spine through the skin of the patient in order to allow the surgeon access to the spine. A flange ring 70 is secured to proximal end 54, and opposite fingers 58a and 58b extend from distal end 56. Fingers 58a, 58b can be sized according to the desired height of the particular disc space and the depth of the disc space into which the outer sleeve 50 is to be inserted. Fingers 58a, 58b maintain the spacing between the adjacent vertebrae during surgical procedures, prevents surrounding tissue and vasculature and from migrating into the disc space, and protects surrounding tissue and vasculature during surgical procedures. In addition, fingers 58a, 58b can be tapered along all or a portion of their length in order to conform to a normal angle between adjacent vertebrae at the instrumented level. In one alternate form, fingers 58a, 58b distract the disc space during insertion therein in lieu of distractor assembly 100.

As shown in FIG. 4, working channel 52 has a figure-eight shape, and sleeve 50 has a wall 51 forming a non-circular perimeter. In the illustrated embodiment, wall 51 has a racetrack shaped perimeter. Other shapes for the perimeter of wall 51 are also contemplated, including elliptical, racetrack shaped, rectangular, or other as would occur to those skilled in the art. Working channel 52 includes a first portion 52a and an adjacent second portion 52b. Each working channel portion 52a and 52b has a truncated circular shape, with the truncated part of the circles adjacent one another. In the illustrated embodiment, the channel 52 defines an overlap region B, indicated by the hatched area in FIG. 4, that is comprised of the area of the truncated portions of the circles forming first portion 52a and second portion 52b. This embodiment of guide sleeve 50 has a reduced profile that minimizes the width of channel 52 between fingers 58a, 58b while, as described further below, providing for bi-lateral implant insertion. Other shapes for working channel 52 are also contemplated, including circular first and second portions that are non-overlapping; elliptical, racetrack shaped, square, or rectangular working channels; working channels formed by adjacent circular guide sleeves; and other working channel shapes as would occur to those skilled in the art.

A distractor assembly 100 includes a first distractor 102 and a second distractor 112 disposed in working channel 52. Distractors 102 and 112 include distractor tips 103 and 113, respectively, positioned between first distraction finger 58a and second distraction finger 58b extending from distal end 56. As shown further in FIG. 7, a lock pin 80 releasably secures distractor assembly 100 to guide sleeve 50. Lock pin 80 includes stem 82 that extends from head 86. Stem 82 includes a plurality of recesses 84a, 84b, 84c formed therealong and a shoulder 88 between recesses 84 and head 86. Recesses 84 receive grommets 85 therein. Recess 84c is illustrated without a grommet 85 for the purposes of clarity.

A cap member 150 is positioned on proximal end 54 of sleeve 50. Cap member 150 is secured to sleeve 50 via a spring clip 90 extending between cap member 150 and flange ring 70. As shown further in FIG. 5, flange ring 70 includes a sleeve member 72 defining a guide sleeve bore 73 extending through flange ring 70. Guide sleeve bore 73 is preferably sized and shaped to substantially correspond to the perimeter of wall 51 and receive guide sleeve 50 in a snug fitting relationship. Flange ring 70 can then be welded, bolted or otherwise secured to guide sleeve 50. A flange member 74 extends outwardly from sleeve member 72 and is positioned at a proximal end of sleeve member 72 so that flange member 74 is aligned with the proximal end opening of sleeve 50. Flange member 74 has a sidewall 75 that includes a groove 76 formed therein. Flange member 74 has a flange extension 78 extending therefrom towards the distal end of sleeve member 72. Flange extension 78 has a lock pin hole 79 extending therethrough and also through sleeve member 72 to communicate with guide sleeve opening 73. When flange ring 70 is properly positioned on proximal end 54 of sleeve 50, lock pin hole 79 is aligned with through-hole 60 formed in guide sleeve 50. Grommets 85 allow selective positioning of lock pin 80 in lock pin hole 79 so that stem 82 extends into or is retracted from a through-hole 60 of distractor assembly 100 (FIG. 3) and locking receptacles 106, 116 of distractors 102, 112 (FIGS. 21, 24) to engage and disengage distractor assembly 100 from guide sleeve 50.

As shown in FIG. 6, spring clip 90 is circular in shape and includes a resilient body 92 extending between first arm 94a and a second arm 94b. Spring clip 90 is made from spring steel or the like. Arms 94a and 94b extend distally outwardly from body 92 and cap member 150 a sufficient distance so that each can be accessed by the surgeon, as shown in FIG. 1. A gap is formed between arms 94a and 94b. Arms 94a and 94b can be positioned on either side of flange extension 78 when instrument 45 is assembled with sufficient space between flange extension 78 and arms 94a and 94b so spring clip 90 can assume a reduced size configuration by applying a force to arms 94a, 94b in the direction indicated by arrows C. In this configuration, body 92 is substantially positioned in groove 76 of flange ring 70, allowing cap member 150 to be removed or placed on flange ring 70. When arms 94a and 94b are released, clip 90 returns to its original shape shown in FIG. 6 and occupies a portion of an inner groove 178 (FIG. 15) formed in cap member 150 and groove 76 of flange ring 70, securing cap member 150 to guide sleeve 50.

Referring now to FIGS. 8–10, cap member 150 will now be described further. Cap member 150 has a housing 152 and an access port 154 alignable with a corresponding one of the working channel portions 52a and 52b. Preferably, access port 154 is aligned by rotating cap member 150 about the proximal end of sleeve 50. However, other techniques are also contemplated herein, including sliding access port 154 between portions 52a and 52b. In the illustrated embodiment of FIG. 1, access port 154 is aligned with working channel portion 52a. Access port 154 provides the surgeon access to at least a portion of working channel 52 to perform surgical procedures. A valve member 156 is positioned substantially inside housing 152, except for, as discussed below, actuators 157a and 157b positioned outside housing 152 to control valve disc 188. An insert member 158 is positioned in housing 152.

Referring further to FIGS. 11–12, housing 152 includes an outer wall 160 and a proximal end wall 161 defining a hollow interior 163. A valve member opening 162 is formed through end wall 161. Housing 152 has a central axis 166 that is substantially aligned with central axis 55 of sleeve 50 when cap member 150 is placed thereon. Valve member opening 162 has a central axis 167 substantially aligned with a center line 53a of first portion 52a of working channel 52 when cap member 150 is secured to sleeve 50 as shown in FIG. 1. Outer wall 160 includes opposite flats 166a and 166b that allow positioning and pivoting operation of actuators 157a and 157b adjacent the outer surface of outer wall 160. As illustrated in FIGS. 9–10, housing 152 has an outer perimeter that is elliptically shaped, similar to the racetrack shaped outer perimeter defined by wall 51 of guide sleeve 50, to minimize the profile of assembly 45. However, other shapes for housing 52, including shapes that are not similar to the shape of guide sleeve 50, are also contemplated. Opposing notches 164a and 164b are formed in the distal end of wall 160. Notches 164a and 164b selectively receive lock pin 80 to provide an indication of proper alignment of cap member 150 on guide sleeve 50.

Referring to FIGS. 13–15, insert member 158 includes an outer wall 170 and a proximal end wall 171 defining a hollow interior 173. A valve member opening 174 is formed through end wall 171. Insert member 158 has a central axis 176 that is substantially aligned with central axis 55 of sleeve 50 when cap member 150 is placed thereon. Valve member opening 174 has a central axis 177 substantially aligned with a center line 53a of first portion 52a of working channel 52 when cap member 150 is secured to sleeve 50 as shown in FIG. 1. A rim 172 extends from outer wall 170 inwardly towards hollow interior 173. A groove 178 is formed in wall 170 between the distal end of insert member 158 and rim 172. Groove 172 receives a portion of body 92 of spring clip 90 to secure cap member 150 to guide sleeve. As best shown in FIG. 9, first fastener 179a and second fastener 179b extend through housing 152 and into rim 172 to secure insert member 158 to housing 152. Groove 178 and wall 170 have a circular shape that corresponds to the shape of flange member 74. Cap member 150 can be rotated about flange ring 70 to position access port 54 in alignment with second portion 52b without removing cap member 150 from guide sleeve 50, thus preserving the insufflated environment of the working space. Opposing notches 175a and 175b are formed in wall 170 opposite end wall 171 and are positioned adjacent notches 164a, 164b, respectively, when insert member 158 and housing 152 are assembled, receiving lock pin 80 and providing an indication of proper alignment of cap member 150 on guide sleeve 50.

Referring now to FIGS. 16–19, valve member 56 will be further described. Valve member 56 includes a proximal end portion 180 and a distal end portion 182 that extends distally from proximal end portion 180. Proximal end portion 180 has an outer dimension d1 that is greater than an outer dimension d2 of distal end portion 182. As shown in FIG. 10, proximal end portion 180 is secured to housing 152 via a first fastener 168a and an elongated second fastener 168b such that proximal end portion 180 is positioned in valve opening 162 of housing 152 and extends proximally from end wall 161. Distal end portion 182 is positioned in valve opening 174 of insert member 158 and extends into hollow interior 173 of insert member 158. Distal end portion 182 has inclined face 184 having a dovetail flange 185 extending therefrom. Inclined face 184 is formed at an angle A with respect to a central axis 186 of valve member 156. In the illustrated embodiment, angle A is about 40 degrees. Values for angle A ranging from 0 to 90 degrees are also contemplated.

Figure 18:
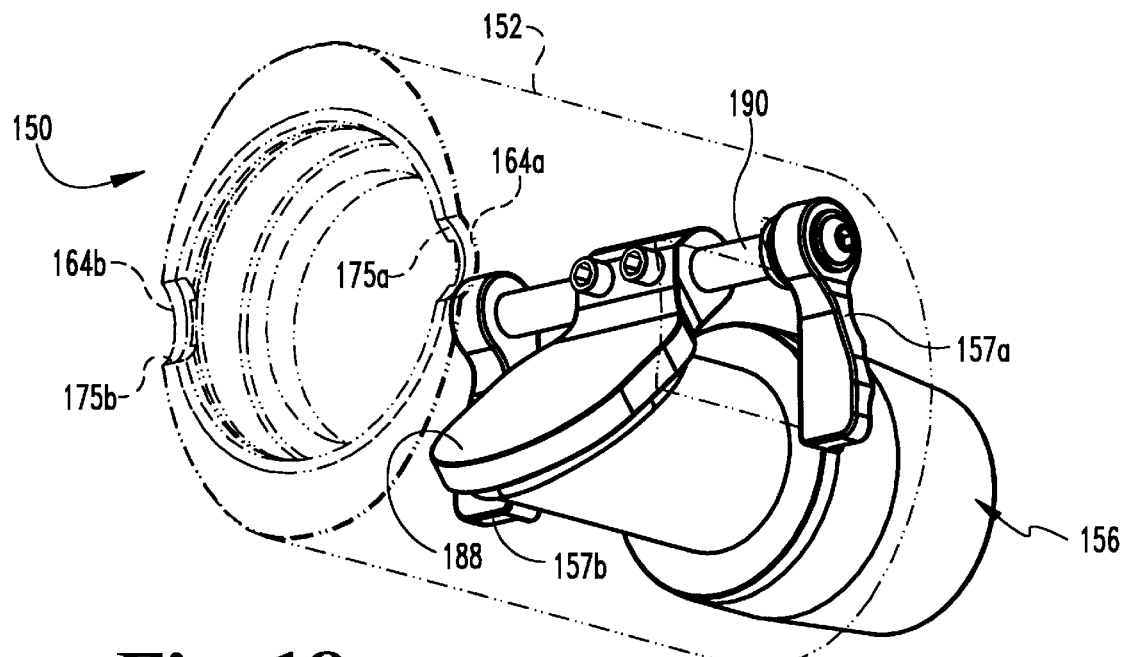
FIG. 18 is a partial hidden line perspective view of the cap member of FIG. 8 with the valve member in a closed position.
Figure 19:
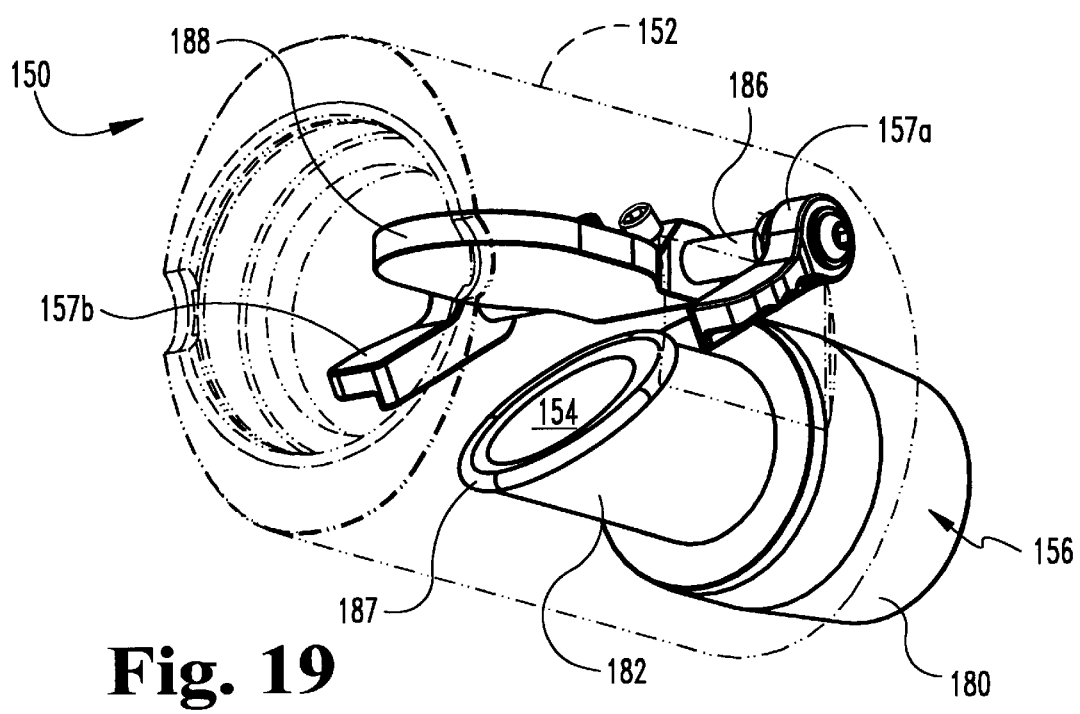
FIG. 19 is a partial hidden line perspective view of the cap member of FIG. 8 with the valve member in an open position.

As shown in FIG. 18, an O-ring 187 (FIG. 19) can be secured to dovetail 185 to provide a sealing interface with valve disc 188 when valve member 156 is closed. Disc 188 is coupled to valve stem 190 extending through housing 152 to opposite actuators 157a and 157b positioned alongside the outer surface of wall 160. Valve member 156 is in a closed condition with actuators 157a, 157b in a first position. In FIG. 19 actuators 157a, 157b are have been rotated distally to a second position that rotates disc 188 distally away from inclined face 184. Preferably, disc 188 is rotated so that it is substantially parallel to central axis 55, clearing access port 154 and allowing insertion of surgical instruments therethrough. Detent mechanisms, friction between actuators 157a, 157b and housing 152, or other mechanisms can be used to releasably maintain actuators 157a, 157b in the above-described first and second positions.

Referring now to FIG. 16, access port 154 extends through valve member 156, and valve member 156 has a central axis 186 that is substantially aligned with centerline 53a of first portion 52a of working channel 52 when cap member 150 is secured to sleeve 50 as shown in FIG. 1. Proximal end portion 182 has an enlarged proximal end opening 189 that extends to a ledge 198. As shown in an enlarged form in FIG. 17, a valve insert 192 is insertable into proximal end opening 189. Valve insert 192 has wall 193 defining a bore 197 extending between a distal face 194 and a proximal face 195. When assembled, distal face 194 abuts ledge 198 with proximal face 195 flush with proximal end wall 191 of upper end portion 180. An O-ring 196 is provided between end face 194 and ledge 198 extending into bore 197. O-ring 196 is sized to sealingly contact a surgical instrument extending through port 154. A grommet made of flexible material or other type of catch can be placed in recess 183 between proximal end portion 180 and valve insert 192 to hold valve insert 192 in position and provide a secure assembly. Sealing member 150 is adaptable to receive a second instrument of different size by removing insert member 192 and inserting a second insert member in end opening 189 having a bore and O-ring sized to sealingly receive the second instrument.

While illustrated as having various components assembled via fasteners, it is also contemplated that cap member 150 can be fabricated from a fewer number of components. For example, housing 152 and insert member 158 could be formed as a single unit. It is also contemplated that the components of cap member 150 are fabricated from surgical grade stainless steel; however, use of other material is not precluded. In one specific form, the valve disc, stem and actuators are fabricated from aluminum.

Referring now to FIGS. 20–22, first distractor 102 will now be further described. First distractor 102 includes distractor tip 103 at a distal end and a shaft 104 extending from tip 103 to a proximal end. Distractor 102 has a length along a central axis 107 such that the proximal end is positioned within assembly 45 when distractor 102 is secured to sleeve 50. As shown in FIG. 22, tip 103 and shaft 104 have a circular shape, and shaft 104 is sized to be slidably received in first portion 52a with central axis 107 substantially aligned with centerline 53a. Adjacent the distal end is a slot 105 and a lock pin receptacle 106. As described further below, slot 105 is configured to couple distractor 102 to a distractor puller, such as distractor puller 220 of FIG. 35. Receptacle 106 receives a portion of lock pin 80 to secure distractor 102 to sleeve 50. Distractor tip 103 includes a rounded nose 103a to ease insertion of tip 103 through tissue and into the disc space. Also provided in the illustrated embodiment is a fin 108 extending from tip 103 towards the upper and the lower vertebral bodies. Fin 108 secures distractor 102 to the vertebral endplates and resists lateral migration of distractor 102 during the surgical procedure.

Referring now to FIGS. 23–25, second distractor 112 will now be further described. Second distractor 112 includes distractor tip 113 at a distal end and a shaft 114 extending from tip 113 to a proximal end. Distractor 112 has a length along a central axis 117 such that the proximal end is positioned within assembly 45 when distractor 112 is secured to sleeve 50. As shown in FIG. 22, tip 113 and shaft 114 have a substantially circular shape, and shaft 114 is sized to be slidably received in second portion 52b with central axis 117 substantially aligned with centerline 53b. Adjacent the distal end is a slot 115 and a lock pin receptacle 116. As described further below, slot 115 is configured to couple distractor 112 to a distractor puller, such as distractor puller 220 of FIG. 35. Receptacle 116 receives a portion of lock pin 80 to secure distractor 112 to sleeve 50. Distractor tip 113 includes a rounded nose 113a to ease insertion of tip 113 through tissue and into the disc space. Also provided in the illustrated embodiment is a fin 118 extending from tip 113 towards the upper and the lower vertebral bodies. Fin 118 secures distractor 112 to the vertebral endplates and resists lateral migration of distractor 112 during the surgical procedure.

In the illustrated embodiment of FIG. 25, distractor 112 has a recessed portion 119 extending along the length of tip 113 and shaft 114. Recessed portion is preferably in the form of a concavely curved surface that receives a portion of the circular distractor 102 when distractors 102, 112 are positioned in guide sleeve 50. This provides a reduced width profile for assembly 45, reducing trauma to and retraction of surrounding tissue and vasculature during the surgical procedure.

While the illustrated embodiment shows a particular type distractor assembly 100, it should be understood that the present invention contemplates various other types of distractor assemblies. For example, the distractor tips need not include fins. In one alternate form, the distal ends of the distractor shafts can be threaded to receive any one of a number of various-sized detachable distractor tips for insertion into the disc space. The appropriate-sized distractor tip is selected according to the vertebral level being instrumented. While not required, progressively larger distractor tips may be sequentially inserted in alternating fashion into the disc space until the adjacent vertebrae are adequately distracted. In another alternate form, the first and second distractors both have a completely circular cross-section and working channel 52 is configured to receive the circular distractors in side-by-side relation. In a further form, the first and second distractors include a nut or other device on the proximal for connecting to a tool for rotating the distractor tip in the disc space. Other variations and forms of distractor assembly 100 are also contemplated as would occur to those skilled in the art.

Referring now to FIGS. 26–29, a reaming sleeve 130 and reamer 140 for preparing the disc space for implant insertion are illustrated. Reaming sleeve 130 includes a tubular member 131 having a bore 134 extending therethrough between a distal end and a proximal end. Sleeve 130 has a central axis 135 and a length between its distal and proximal ends sufficient to extend from the vertebral bodies through sleeve 50 and cap member 150 with flange 133 adjacent to or abutting the proximal end wall 191 of valve member 156. A pair of opposite spikes 132a and 132b extend from the distal end of tubular member 131, and are provided to engage a corresponding one of the vertebral bodies V1 and V2 with sleeve 130 placed through working channel 52 of guide sleeve 50, holding sleeve 130 in place during reaming of the disc space. A driving force can be applied to flange 133 to drive spikes 132a, 132b into vertebral bodies V1, V2.

A reamer 140 has a shaft 141 extending between cutting head 142 at a distal end and a Hudson end connector 143 at a proximal end for connection to a T-handle or the like. Shaft 141 has depth markings 145 to monitor the reaming depth. Shaft 141 has a central axis 145 that is substantially aligned with central axis 135 of sleeve 130 when reamer 140 is placed through bore 134. Central axis 135 and central axis 145 are substantially aligned with center line 53a or 53b when placed through a corresponding one of first portion 52a or second portion 52b of guide sleeve 50.

Shaft 141 can be sized to contact the wall inner 134a of bore 134, allowing sleeve 130 to serve as a guide for reamer 140. As shown in further detail in FIG. 29, cutting head 142 includes a bore 144 and a number of helical blades 146. Bore 144 extends between distal end opening 144a and side opening 144b. A cutout 149 in bore 144 creates openings 148 in communication with bore 144. Reamed material from the disc space is deposited into bore 144 through openings 148 and evacuated through side opening 144b.

Referring now to FIGS. 30 and 31, an implant inserter 200 and inserter sleeve 210 are illustrated. Inserter 200 includes a shaft 201 having a central axis 205 extending between implant holder 202 at a distal end and Hudson connector 203 at a proximal end that can be connected to a T-handle or the like. External threads 204 are provided adjacent the proximal end. Implant holder 202 includes first extension 207a and opposite second extension 207b extending distally from a head 206 for gripping an implant therebetween. Head 206 further includes projection 206a insertable into an end receptacle of an implant (not shown.) Holder 202 includes an enlarged shaft portion 208 extending from shaft 201 to head 206. Enlarged shaft portion includes ramped portion 208a adjacent head 206 that increases in diameter from enlarged portion 208 to head 206. A slot 209 is formed through head 202 and enlarged portion 208 to allow deflection of extensions 207a, 207b towards one another, facilitating gripping of the implant therebetween.

Inserter sleeve 210 has a central axis 215 and includes a tubular member 211 defining a bore 217 extending between a proximal end and a distal end of sleeve 210. Depth markings 216 are provided adjacent the proximal end of sleeve 210. A first bushing 212 is inserted in bore 217 at the distal end of sleeve 210 and second bushing 213 is inserted in bore 217 and extends from the proximal end of sleeve 210. Bore 217 extends through first bushing 212 and second bushing 213. First bushing 212 includes ramped portion 212a mating with ramped portion 208a of holder 202 when inserter 200 is placed through bore 217. Second bushing 213 includes internal threads 214 threadingly receiving threads 204 of inserter 200. As inserter 200 is threaded proximally into bore 217 of sleeve 210, first bushing 212 compresses holder 202 to secure the implant between first and second extensions 207a and 207b.

A surgical procedure using instrument assembly 45 will now be described. In FIG. 32 instrument assembly 45 is assembled prior to insertion to the disc space and impactor cap 240 placed on the proximal end of cap member 150. Stem 82 of lock pin 80 is inserted through lock pin hole 79 and into lock pin receptacles 106, 116 of dilators 102, 112. Shoulder 88 is positioned adjacent extension 78 and partially received in notches 164a, 175a, preventing rotation of cap member 150 and providing an indication of proper alignment of cap member 150 on guide sleeve 50. Valve member 156 is in a closed position as shown in FIG. 18. Impactor cap 240 transfers a driving force from a hand, mallet, slap hammer, or the like to instrument assembly 45 to drive distractor tips 103, 113 and fingers 58a, 58b into disc space D.

Impactor cap 240 includes recessed gripping elements 242 to facilitate handling of cap 240. As shown in FIG. 33, impactor cap 240 includes an outer wall 244 and end wall 246 defining a hollow interior 248. A bearing wall 249 is formed in hollow interior 248 that abuts proximal end wall 161 of housing 152. A well 250 is formed in bearing wall 249 to receive a part of proximal end portion 180 of valve member 156 extending proximally of end wall 161. When impactor cap 240 is placed on cap member 150, well 250 has a central axis 254 that is substantially aligned with central axis 186 of valve member 156, and impactor cap 240 has a central axis 252 that is substantially aligned with central axis 55 of sleeve 50.

In order for instrument assembly to be positioned adjacent the disc space, it is first necessary to retract the tissue between the skin level and the subject disc space using any one of a known number of techniques and/or instruments. Techniques for preparing the surgical site and the disc space for entry via an anterior approach, including discectomy procedures and midline marking procedures, are known to those skilled in the art. Examples of such techniques are disclosed in PCT Publication No. WO 97/30666, which is incorporated herein by reference in its entirety.

It may be necessary for the surgeon to slightly twist or wrest instrument assembly 45 to advance it through the skin and tissue to disc space D. Instrument assembly 45 should be properly located with respect to the disc space, and insertion can be performed, monitored, and/or confirmed with radiographic imaging or direct visualization. When the proximal end of the assembly is positioned adjacent the disc space and impactor cap 240 is mounted on cap member 150, a driving force from a hand, mallet, slap hammer, or the like is applied to impactor cap 240 to drive distractor tips 103, 113 and fingers 58a, 58b into disc space D.

The configuration of outer sleeve 50 allows surgical procedures to be performed within disc space D in order to, for example, prepare the disc space and insert vertebral implants at a left bilateral location $I_L$ and a right bilateral location $I_R$ (FIG. 1a.) It should be appreciated sleeve 50 allows the procedures to be performed in the disc space D at these bilateral locations through working channel 52 without requiring manipulation of the sleeve 50 between the bilateral locations, although procedures involving manipulation of sleeve 50 through the skin to alternate locations are not precluded by the present invention.

As shown in FIG. 34, once assembly 45 is in the desired position in disc space D, impactor cap 240 is removed. In order to release distractor assembly 100 from guide sleeve 50, lock pin 80 is pulled upward until stem 82 is no longer positioned in lock pin receptacles 106, 116, disengaging dilators 102, 112 from sleeve 50. Grommets 85 maintain the positioning of lock pin 80 with shoulder 88 positioned outside notches 164a, 175a, allowing rotation of cap member 150 about flange ring 70. Preferably, lock pin 80 remains positioned in hole 79 so that stem 82 serves as a guide for proper alignment of cap member 150. Actuators 157a, 157b are rotated proximally to rotate disc 188 and open valve member 156, as shown in FIG. 19.

As shown in FIG. 34, once assembly 45 is in the desired position in disc space D, impactor cap 240 is removed. In order to release distractor assembly 100 from guide sleeve 50, lock pin 80 is pulled upward until stem 82 is no longer positioned in lock pin receptacles 106, 116, disengaging dilators 102, 112 from sleeve 50. Grommets 85 maintain the positioning of lock pin 80 with shoulder 88 positioned outside notches 164a, 174a, allowing rotation of cap member 150 about flange ring 70. Preferably, lock pin 80 remains positioned in hole 79 so that stem 82 serves as a guide for proper alignment of cap member 150. Actuators 157a, 157b are rotated proximally to rotate disc 188 and open valve member 156, as shown in FIG. 19.

Once valve member 156 is opened, distractor remover 220 is inserted through port 154 and engaged to notch 105 of distractor 102, as shown in FIG. 34a. As shown in FIG. 35, distractor puller 220 has a shaft 222 extending between a Hudson connector 226 at a proximal end and a stem 226 at a distal end. Stem 226 has a trough 227 that receives a catch 224 therein. Catch 224 has a raised portion 225 and is pivotally engaged in trough 227 via a pin 228. A spring 230 biases catch 224 upwardly. Catch 224 is pushed into trough 227 as stem 226 is inserted a sufficient amount into the proximal end of shaft 104 until raised portion 225 is pushed by spring 230 into in notch 105, coupling puller 220 to distractor 102. A remover tool, such as remover 260, is coupled to connector 226 of puller 220. Remover 260 has a shaft 262 extending between connector 264 and a stop member 266. A slide 268 is slidably disposed on shaft 262, and is moved proximally and distally on shaft 262 to impact stop member 266 and remove distractor 102 from the disc space D. Catch 226 is depressed into trough 227 to remove puller 220 from notch 105. Once distractor 102 is removed, valve member 156 can be moved to the closed position to maintain the sealed environment.

Referring now to FIGS. 36 and 36a, distractor 102 is removed, valve member 156 is moved to its open position, and reamer sleeve 130 is inserted into first portion 52a of working channel 52. A mallet or other device can be used to apply a driving force against flange 133 and drive spikes 132a and 132b in vertebral bodies V1 and V2, respectively. Once sleeve 130 is securely positioned, reamer 140 is inserted into bore 134 as shown in FIGS. 37 and 37a. A T-handle 270 is coupled to Hudson connector 143, allowing the surgeon to rotate head 142 to ream material from disc space D at a first bi-lateral location. The depth of reaming in disc space D can be determined and monitored via radiographic imaging and/or monitored via depth markings 145, direct visualization, radiographic imaging or the like. When reaming is complete, sleeve 130 and reamer 140 are removed from working channel 52 and valve member 156 can be moved to its closed position to maintain the sealed environment.

Figure 38:
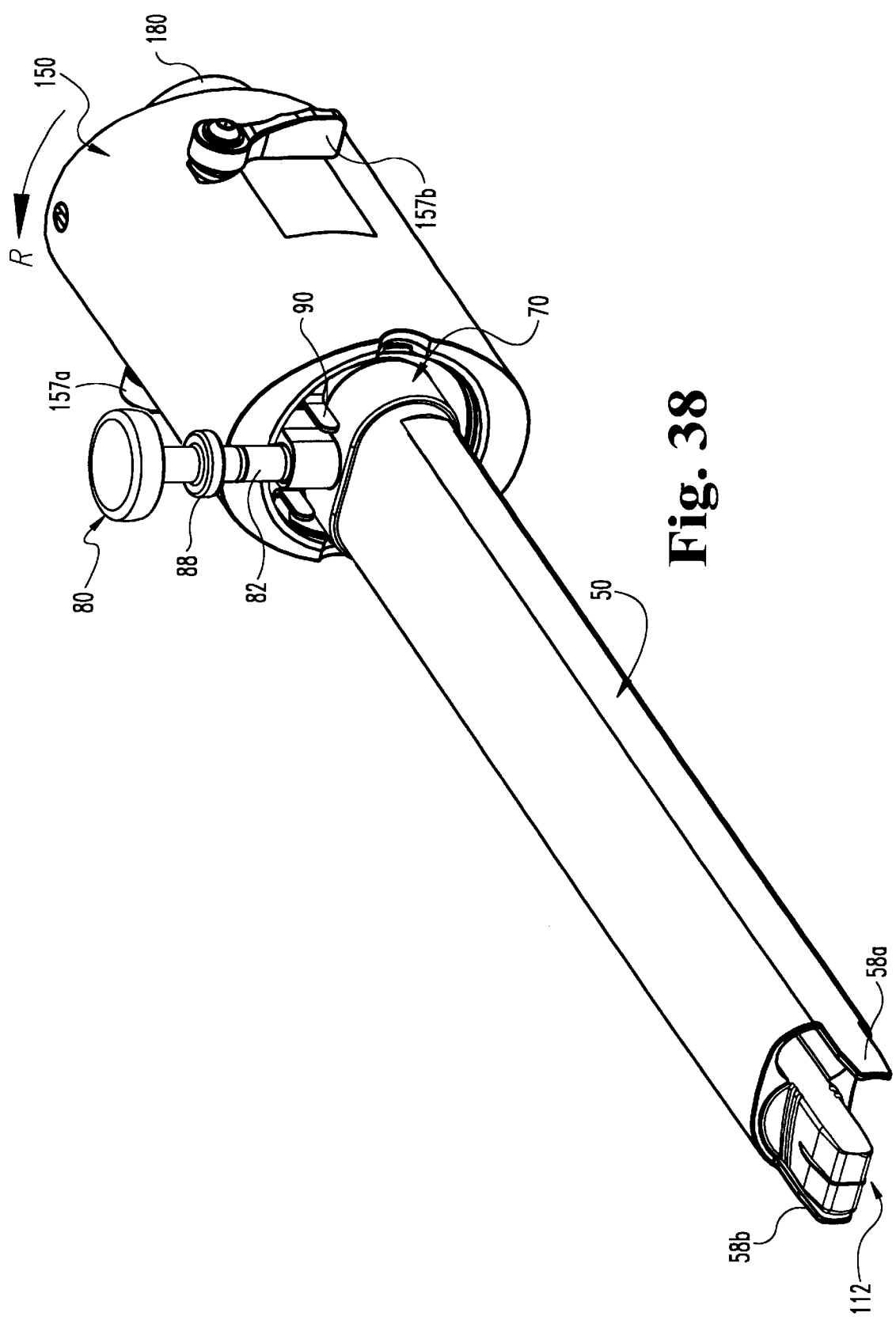
FIG. 38 is a perspective view of the surgical instrument assembly of the present invention with the first distractor and reaming sleeve removed and the cap member being rotated for alignment with the second distractor.

Referring now to FIG. 38, cap member 150 is being rotated as indicated by arrow "R" to align port 154 with second portion 52b of working channel 52. During rotation, valve member 156 is closed and the distal end of housing 152 is adjacent to or abuts stem 82 of lock pin 80. This helps maintain proper positioning and alignment of cap member 150 during rotation thereof. If necessary, spring clip 90 can be compressed via arms 94a and 94b to facilitate rotation of cap member 150. Once port 154 is aligned with second portion 152b, second distractor 112 may be removed in a manner similar to that described above with respect to first distractor 102. Distraction of disc space D is maintained evenly by fingers 58a and 58b. Of course, cap member 150 may also be rotated in the direction opposite arrow R to reposition access port 154.

Referring now to FIGS. 39 and 39a, reaming sleeve 130 and reamer 140 are inserted through second portion 52b of working channel 52. In a manner similar to that described above with respect to FIGS. 37 and 37a, disc space D is reamed at a second bilateral location adjacent the first bilateral location to prepare it for insertion of an implant therein. Once the disc space is reamed, reaming sleeve 130 and reamer 140 are withdrawn from sleeve 50 and valve member 156 closed.

Referring now to FIGS. 40 and 40a, an implant 280 is secured to implant inserter 200 and inserter sleeve 210. Valve member 156 is opened and implant 280 is inserted through second portion 52b along with implant inserter 200 and inserter sleeve 210. T-handle 270 is secured to Hudson connector 203, and implant 280 is threaded to the desired depth in disc space D in the second bilateral location. The depth of insertion in disc space D can be determined and monitored via depth markings 216, direct visualization, radiographic imaging or the like. Inserter 200 and sleeve 210 are uncoupled to release extensions 207a and 207b from implant 280 and withdrawn form sleeve 50. Valve member 156 is then closed. In one form, implant 280 can be provided with a recessed portion similarly shaped as the recessed portion 119 described above with respect to tip 113 of second distractor 112. The recessed portion of implant 280 faces the reamed disc space at the first bilateral location, and the recessed portion receives a portion of second implant 290, reducing the overall width of the disc space occupied by implants 280, 290.

Referring now to FIGS. 41 and 41a, a second implant 290 is secured to implant inserter 200 and inserter sleeve 210. Valve member 156 is opened and implant 290 is inserted through first portion 52a of working channel 52 along with implant inserter 200 and inserter sleeve 210. T-handle 270 is secured to Hudson connector 203, and implant 290 is threaded to the desired depth in disc space D. The depth of insertion in disc space D can be determined and monitored via depth markings 216, direct visualization, radiographic imaging or the like. Inserter 200 and sleeve 210 are uncoupled to release extensions 207a and 207b from implant 290 and withdrawn from sleeve 50. Sleeve 50 may then be withdrawn from disc space D and the entry wound closed using standard surgical techniques.

Variations in the above described surgical technique are also contemplated. For example, all the procedures can be completed through first working channel portion 52a, including implant insertion, prior to positioning access port 154 with second portion 154b. While certain instruments have been described for use assembly 45, it should be understood that the present invention is not limited to use of such instruments and the use of any such instruments with assembly 45 as would occur to those skilled in the art are also contemplated.

It should be appreciated that disc space D can be prepared for bilateral implant insertion without movement or manipulation of guide sleeve 50 after the fingers 58a and 58b are positioned within disc space D since the surgeon has access to each of the bilateral locations through working channel 52. It should also be appreciated that disc space D may be tapped to facilitate insertion of threaded implants. It should be further appreciated that the implants can be provided with osteogenic or bone growth material to promote fusion, or that such material can be placed directly into disc space D. In a further form, it is contemplated that the implants are not threaded, but rather are configured for pushing or driving into the prepared disc space.

While the invention has been illustrated and described in detail in the drawings and foregoing description, the same is to be considered as illustrative and not restrictive in character, it being understood that only the preferred embodiments has been shown and described and that all changes and modifications the come within the spirit of the invention are desired to be protected.

What is claimed is:

1. A method for performing a surgical procedure in a disc space between adjacent vertebrae of a patient, comprising:

accessing the disc space;

providing an instrument assembly including a sleeve having a distal end and an opposite proximal end, the sleeve defining a substantially sealable working channel between the distal and proximal ends, the working channel having a first portion and an adjacent second portion, further including a cap member secured to the proximal end of the sleeve, the cap member having a sealable access port;

advancing the sleeve in the patient until the proximal end of the sleeve is positioned adjacent the disc space;

positioning the cap member with the access port aligned with the first portion of the working channel with the working channel substantially sealed; and positioning the cap member with the access port aligned with the second portion of the working channel with the working channel substantially sealed.

2. The method according to claim 1, further comprising:

opening the access port with the access port aligned with the first portion;

performing a first procedure through the first portion of the working channel through the opened access port;

sealing the access port;

opening the access port after positioning the cap member with the access port aligned with the second portion; and performing a second procedure in the second portion of the working channel through the opened access port.

3. The method of claim 1, wherein accessing the disc space includes performing a discectomy.

4. The method of claim 1, wherein positioning the cap member includes rotating the cap member about the proximal end of the sleeve to align the access port with the second portion of the working channel.

5. The method of claim 4, wherein providing the instrument assembly includes providing a guide sleeve having a flange ring at the proximal end secured to the cap member.

6. The method of claim 1, wherein the sleeve includes opposite fingers extending from the distal end into the disc space.

7. The method of claim 6, wherein advancing the sleeve includes impacting the sleeve to insert the opposite fingers into the disc space.

8. The method of claim 6, wherein providing the instrument assembly further comprises providing a first distractor and a second distractor, each positioned in a corresponding one of the first and second portions of the working channel and secured to the sleeve, each of the first and second distractors including a distractor tip at a distal end adjacent one of the opposite fingers and a shaft extending from the distractor tip to a proximal end.

9. The method of claim 8, wherein advancing the sleeve includes impacting the opposite fingers and the distractor tips into the disc space to distract the disc space.

10. The method of claim 9, further comprising opening the access port and removing the first distractor from the first portion of the working channel before positioning the cap member.

11. The method of claim 10, further comprising:
  inserting a reaming sleeve into the first portion of the working channel through the opened access port; and
  inserting a reamer through the reaming sleeve to ream a first disc space location.

12. The method of claim 11, wherein the reaming sleeve has opposite spikes for engaging the adjacent vertebrae.

13. The method of claim 11, further comprising:
  removing the reaming sleeve and reamer from the first portion of the working channel; and
  opening the access port and removing the second distractor from the second portion of the working channel after positioning the cap member.

14. The method of claim 13, further comprising:
  inserting a reaming sleeve into the second working channel portion through the access port; and
  inserting a reamer through the reaming sleeve to ream a second disc space location adjacent the first disc space location.

15. The method according to claim 14, further comprising:
  removing the reaming sleeve and the reamer; and
  inserting a first implant into the second disc space location.

16. The method according to claim 15, further comprising after inserting the first implant:
  positioning the cap member with the access port aligned with the first portion of the working channel portion with the working channel substantially sealed.

17. The method of to claim 16, further comprising inserting a second implant into the first disc space location after inserting the first implant.

18. An apparatus for performing surgical procedures in a disc space between adjacent vertebrae of a patient, comprising:
  a sleeve having a distal end and proximal end, said sleeve defining a working channel therethrough, said working channel including:
    a first portion and an adjacent second portion, said first and second portions each configured to receive surgical instruments therethrough; and
  a cap member substantially sealing said working channel secured to said sleeve at said proximal end, said cap member having an access port alignable with a corresponding one of said first or second portions, said cap member movable with respect to said sleeve in substantial sealing engagement therewith to align said access port with the other of said first and second portions.

19. The apparatus of claim 18, wherein said working channel remains sealed as said cap member is rotated about said sleeve to align said access port.

20. The apparatus of claim 18, wherein said cap member includes a valve member having a valve disc for sealing said working channel, said valve disc coupled to at least one actuator for opening and closing said access port.

21. The apparatus of claim 20, wherein said valve member includes:
  a stem extending through and mounted to said cap member and coupled to said valve disc;
  said least one actuator coupled to said stem outside said cap member, wherein said actuator is pivotable from a closed position whereby said valve disc substantially closes said access port to an open position whereby said valve disc does not substantially close said access port.

22. The apparatus of claim 21, wherein said actuator rotates said stem to move said valve disc between said closed position and said open position.

23. The apparatus of claim 18, wherein said cap member includes an O-ring extending into said access port, said O-ring sealingly receiving surgical instruments extending through said access port to maintain said substantially sealed working channel.

24. The apparatus of claim 18, wherein said cap member includes:
  a valve member having a valve disc for sealing said working channel, said valve disc coupled to at least one actuator for opening and closing said access port; and
  an O-ring extending into said access port, said O-ring sealingly receiving surgical instruments extending through said access port to maintain said substantially sealed working channel.

25. The apparatus of claim 24, wherein said valve member includes:
  a stem extending through and mounted to said cap member and coupled to said valve disc;
  said least one actuator coupled to said stem outside said cap member, wherein said actuator is pivotable from a closed position whereby said valve disc substantially closes said access port to an open position whereby said valve disc does not substantially close said access port.

26. The apparatus of claim 25, wherein said actuator rotates said stem to move said valve disc between said closed position and said open position.

27. The apparatus of claim 18, wherein said sleeve includes a pair of opposite fingers extending from said distal end for insertion in a distracted disc space.

28. The apparatus of claim 18, wherein said first portion of said working channel allows a surgical procedure to be performed at a first disc space location and said second portion of said working channel allows a surgical procedure to be performed at a second disc space location.

29. The apparatus of claim 28, wherein said working channel has a figure eight shape formed by said first and second portions.

30. The apparatus of claim 28, wherein each of said first and second portions has a truncated circular shape, wherein said truncated portions of the circle are positioned adjacent one another.

31. The apparatus of claim 18, wherein said sleeve includes a flange ring at said proximal end and said cap member is secured to said flange ring.

32. The apparatus of claim 31, wherein said sleeve has a racetrack shaped perimeter and said flange ring has a circular shaped perimeter.

33. The apparatus of claim 32, wherein said flange ring includes a sleeve member having a racetrack shaped inner bore positioned about said racetrack shaped perimeter of said sleeve.

34. The apparatus of claim 31, wherein said access port is aligned with said first or second portion by rotating said cap member about said flange ring.

35. The apparatus of claim 34, wherein:
  said cap member has an inner circular insert member that includes an inner groove adjacent a distal end thereof;
  said flange ring includes a sidewall forming an outer perimeter, said sidewall having a groove formed therein; and
  said cap member being secured to said flange ring by a spring clip extending between said sidewall groove and said inner groove.

36. The apparatus of claim 18, further comprising a pair of distractors, each distractor disposed in a corresponding one of said first and second portions, said pair of distractors releasably coupled to said sleeve, each of said distractors having a distractor tip for distracting the disc space when inserted therein.

37. The apparatus of claim 36, further comprising an impactor cap positionable over said cap member to receive a driving force to insert said distractors in the disc space with said working channel sealed.

38. An apparatus for performing surgical procedures in a disc space between adjacent vertebrae of a patient, comprising:

a sleeve having a longitudinal axis and working channel extending between a distal end and a proximal end along said longitudinal axis, said working channel including a first portion substantially aligned with said longitudinal axis and an adjacent second portion substantially aligned with said longitudinal axis; and a valve housing sealingly engaged to said proximal end of said sleeve, said valve housing having an access port for selective access to said working channel, said access port alignable with a corresponding one of said first and second portions of said working channel while said working channel remains sealed by rotating said valve housing about said sleeve.

39. The apparatus of claim 38, wherein said first and second portions are in communication with one another.

40. The apparatus of claim 38, wherein said valve housing seals both said first and second portions.

41. The apparatus of claim 38, wherein said access port is alignable by moving said valve housing with respect to said sleeve.

42. The apparatus of claim 41, wherein said valve housing is moved by rotating said valve housing about said proximal end of said sleeve.

43. The apparatus of claim 38, wherein said valve housing is removable.

44. The apparatus of claim 38, wherein said sleeve includes a flange ring at said proximal end and said valve housing is secured to said flange ring.

45. The apparatus of claim 44, wherein said sleeve has a racetrack shaped perimeter and said flange ring has a circular shaped perimeter.

46. The apparatus of claim 38, further comprising a pair of distractors, each distractor disposed in a corresponding one of said first and second portions of said sleeve, said pair of distractors releasably coupled to said sleeve, each of said distractors having a distractor tip for distracting the disc space when inserted therein.

47. The apparatus of claim 46, further comprising an impactor cap positionable over said valve housing to receive a driving force to insert said distractors in the disc space with said working channel sealed.

48. An apparatus for performing surgical procedures in a disc space between adjacent vertebrae of a patient, comprising:

a sleeve having a longitudinal axis and working channel extending between a distal end and a proximal end along said longitudinal axis, said working channel including a first portion substantially aligned with said longitudinal axis for performing a first procedure therethrough at a first location and an adjacent second portion substantially aligned with said longitudinal axis for performing a second procedure therethrough at a second location; and a housing secured to said proximal end of said sleeve, said housing including a sealable access port for accessing said working channel, said access port movable between said first and second portions of said working channel while said working channel remains sealed.

49. The apparatus of claim 48, wherein said sleeve includes a flange ring at said proximal end and said housing is secured to said flange ring.

50. The apparatus of claim 49, wherein said sleeve has a racetrack shaped perimeter and said flange ring has a circular shaped perimeter.

51. The apparatus of claim 50, wherein said flange ring includes a sleeve member having a racetrack shaped inner bore positioned about said racetrack shaped perimeter of said sleeve.

52. The apparatus of claim 49, wherein said access port is aligned with said first or second portion by rotating said housing about said flange ring.

53. The apparatus of claim 48, wherein said housing includes a valve member having a valve disc coupled to at least one actuator for opening and closing said access port.

54. The apparatus of claim 48, further comprising a pair of distractors, each distractor disposed in a corresponding one of said first and second portions of said sleeve, said pair of distractors releasably coupled to said sleeve, each of said distractors having a distractor tip for distracting the disc space when inserted therein.

55. The apparatus of claim 54, further comprising an impactor cap positionable over said housing to receive a driving force to insert said distractors in the disc space with said working channel sealed.

56. An apparatus for performing surgical procedures in a disc space between adjacent vertebrae of a patient, comprising:

a sleeve having a longitudinal axis and working channel extending between a distal end and a proximal end along said longitudinal axis, said working channel including a first portion substantially aligned with said longitudinal axis and an adjacent second portion substantially aligned with said longitudinal axis; and a valve housing sealing engaged to said proximal end of said sleeve, said valve housing having an access port for selective access to said working channel, said access port alignable with a corresponding one of said first and second portions of said working channel by moving said valve housing with respect to said sleeve while said working channel remains sealed.

57. The apparatus of claim 56, wherein said first and second portions are in communication with one another.

58. The apparatus of claim 56, wherein said valve housing seals both said first and second portions.

59. The apparatus of claim 56, wherein said valve housing is moved by rotating said valve housing about said proximal end of said sleeve.

60. The apparatus of claim 56, wherein said valve housing is removable.

61. An apparatus for performing surgical procedures in the disc space between adjacent vertebrae of a patient, comprising:

a sleeve having a distal end and proximal end, said sleeve defining a working channel therethrough, said working channel including:

a first portion and an adjacent second portion, said first and second portions each configured to receive surgical instruments therethrough; and a cap member substantially sealing said working channel secured to said sleeve at said proximal end, said cap member having an access port alignable with a corresponding one of said first or second portions, said cap member movable with respect to said sleeve to align said access port with the other of said first and second portions, wherein said cap member includes a valve member having a valve disc for sealing said working channel, said valve disc coupled to at least one actuator for opening and closing said access port.

62. The apparatus of claim 61, wherein said working channel remains sealed during movement of said cap member to align said access port.

63. The apparatus of claim 61, wherein said valve member includes:
   a stem extending through and mounted to said cap member and coupled to said valve disc; and
   said least one actuator coupled to said stem outside said cap member, wherein said actuator is pivotable from a closed position whereby said valve disc substantially closes said access port to an open position whereby said valve disc does not substantially close said access port.

64. The apparatus of claim 63, wherein said actuator rotates said stem to move said valve disc between said closed position and said open position.

65. The apparatus of claim 61, wherein said cap member includes an O-ring extending into said access port, said O-ring sealingly receiving surgical instruments extending through said access port to maintain said substantially sealed working channel.

66. The apparatus of claim 65, wherein said actuator rotates said stem to move said disc between said closed position and said open position.

67. The apparatus of claim 61, wherein said sleeve includes a pair of opposite fingers extending from said distal end for insertion in a distracted disc space.

68. The apparatus of claim 61, wherein said first portion of said working channel allows a surgical procedure to be performed at a first disc space location and said second portion of said working channel allows a surgical procedure to be performed at a second disc space location.

69. The apparatus of claim 61, wherein said working channel has a figure eight shape formed by said first and second portions.

70. The apparatus of claim 61, wherein each of said first and second portions has a truncated circular shape, wherein said truncated portions of the circle are positioned adjacent one another.

71. The apparatus of claim 61, wherein said sleeve includes a flange ring at said proximal end and said cap member is secured to said flange ring.

72. The apparatus of claim 71, wherein said sleeve has a racetrack shaped perimeter and said flange ring has a circular shaped perimeter.

73. The apparatus of claim 72, wherein said flange ring includes a sleeve member having a racetrack shaped inner bore positioned about said racetrack shaped perimeter of said sleeve.

74. The apparatus of claim 71, wherein said access port is aligned with said first or second portion by rotating said cap member about said flange ring.

75. The apparatus of claim 74, wherein:
   said cap member has an inner circular insert member that includes an inner groove adjacent a distal end thereof;
   said flange ring includes a sidewall forming an outer perimeter, said sidewall having a groove formed therein; and
   said cap member being secured to said flange ring by a spring clip extending between said sidewall groove and said inner groove.

76. An apparatus for performing surgical procedures in the disc space between adjacent vertebrae of a patient, comprising:
   a sleeve having a distal end and proximal end, said sleeve defining a working channel therethrough, said working channel including:
      a first portion and an adjacent second portion, said first and second portions each configured to receive surgical instruments therethrough; and
   a cap member substantially sealing said working channel secured to said sleeve at said proximal end, said cap member having an access port alignable with a corresponding one of said first or second portions, said cap member movable with respect to said sleeve to align said access port with the other of said first and second portions, wherein said cap member includes:
      a valve member having a valve disc for sealing said working channel, said valve disc coupled to at least one actuator for opening and closing said access port; and
   an O-ring extending into said access port, said O-ring sealingly receiving surgical instruments extending through said access port to maintain said substantially sealed working channel.

77. The apparatus of claim 76, wherein said working channel remains sealed during movement of said cap member to align said access port.

78. The apparatus of claim 76, wherein said valve member includes:
   a stem extending through and mounted to said cap member and coupled to said valve disc;
   said least one actuator coupled to said stem outside said cap member, wherein said actuator is pivotable from a closed position whereby said valve disc substantially closes said access port to an open position whereby said valve disc does not substantially close said access port.

79. The apparatus of claim 78, wherein said actuator rotates said stem to move said valve disc between said closed position and said open position.

80. The apparatus of claim 76, wherein said first portion of said working channel allows a surgical procedure to be performed at a first disc space location and said second portion of said working channel allows a surgical procedure to be performed at a second disc space location.

81. The apparatus of claim 76, wherein said sleeve includes a flange ring at said proximal end and said cap member is secured to said flange ring.

82. The apparatus of claim 81, wherein said sleeve has a racetrack shaped perimeter and said flange ring has a circular shaped perimeter.

83. The apparatus of claim 82, wherein said flange ring includes a sleeve member having a racetrack shaped inner bore positioned about said racetrack shaped perimeter,of said sleeve.

84. The apparatus of claim 81, wherein said access port is aligned with said first or second portion by rotating said cap member about said flange ring.

85. An apparatus for performing surgical procedures in the disc space between adjacent vertebrae of a patient, comprising:
   a sleeve having a distal end and proximal end, said sleeve defining a working channel therethrough, said working channel including:
      a first portion and an adjacent second portion, said first and second portions each configured to receive surgical instruments therethrough; and a cap member substantially sealing said working channel secured to said sleeve at said proximal end, said cap member having an access port alignable with a corresponding one of said first or second portions, said cap member movable with respect to said sleeve to align said access port with the other of said first and second portions, wherein said sleeve includes a flange ring at said proximal end and said cap member is secured to said flange ring, said sleeve having a racetrack shaped perimeter and said flange ring having a circular shaped perimeter.

86. The apparatus of claim 85, wherein said working channel remains sealed during movement of said cap member to align said access port.

87. The apparatus of claim 85, wherein said cap member includes a valve member having a valve disc for sealing said working channel, said valve disc coupled to at least one actuator for opening and closing said access port.

88. The apparatus of claim 87, wherein said valve member includes:
- a stem extending through and mounted to said cap member and coupled to said valve disc;
- said least one actuator coupled to said stem outside said cap member, wherein said actuator is pivotable from a closed position whereby said valve disc substantially closes said access port to an open position whereby said valve disc does not substantially close said access port.

89. The apparatus of claim 88, wherein said actuator rotates said stem to move said valve disc between said closed position and said open position.

90. The apparatus of claim 85, wherein said cap member includes an O-ring extending into said access port, said O-ring sealingly receiving surgical instruments extending through said access port to maintain said substantially sealed working channel.

91. The apparatus of claim 85, wherein said first portion of said working channel allows a surgical procedure to be performed at a first disc space location and said second portion of said working channel allows a surgical procedure to be performed at a second disc space location.

92. The apparatus of claim 85, wherein said flange ring includes a sleeve member having a racetrack shaped inner bore positioned about said racetrack shaped perimeter of said sleeve.

93. The apparatus of claim 85, wherein said access port is aligned with said first or second portion by rotating said cap member about said flange ring.

94. The apparatus of claim 85, wherein:
- said cap member has an inner circular insert member that includes an inner groove adjacent a distal end thereof;
- said flange ring includes a sidewall forming said circular shaped perimeter, said sidewall having a groove formed therein; and
- said cap member being secured to said flange ring by a spring clip extending between said sidewall groove and said inner groove.

* * * * *